United States Patent
Chin et al.

(10) Patent No.: US 9,689,780 B2
(45) Date of Patent: Jun. 27, 2017

(54) APPARATUS AND METHODS FOR ALIQUOTTING FROZEN SAMPLES

(71) Applicant: CryoXtract Instruments, LLC, Boston, MA (US)

(72) Inventors: Larry Chin, Needham, MA (US); Todd Basque, Danvers, MA (US)

(73) Assignee: CRYOXTRACT INSTRUMENTS, LLC, Boston, MA (US)

( * ) Notice: Subject to any disclaimer, the term of this patent is extended or adjusted under 35 U.S.C. 154(b) by 660 days.

(21) Appl. No.: 13/950,170

(22) Filed: Jul. 24, 2013

(65) Prior Publication Data

US 2014/0053664 A1  Feb. 27, 2014

Related U.S. Application Data

(60) Provisional application No. 61/784,753, filed on Mar. 14, 2013, provisional application No. 61/675,016, filed on Jul. 24, 2012.

(51) Int. Cl.
*G01N 1/08* (2006.01)
*G01N 1/42* (2006.01)

(52) U.S. Cl.
CPC ............... *G01N 1/08* (2013.01); *G01N 1/42* (2013.01)

(58) Field of Classification Search
CPC .................................. G01N 1/08; G01N 1/42
USPC ........................................ 73/864.44, 864.45
See application file for complete search history.

(56) References Cited

U.S. PATENT DOCUMENTS

| | | | |
|---|---|---|---|
| 2,435,608 A | 2/1948 | Sanford et al. |
| 2,987,922 A | 6/1961 | Harrington |
| 4,149,414 A | 4/1979 | Walker |
| 5,154,087 A | 10/1992 | Wenshau et al. |
| 6,689,087 B2 | 2/2004 | Pal et al. |
| 6,910,887 B2 | 6/2005 | Van Den Houdt |

(Continued)

FOREIGN PATENT DOCUMENTS

| | | |
|---|---|---|
| DE | 20021405 U1 | 3/2001 |
| EP | 0999340 A2 | 5/2000 |

(Continued)

OTHER PUBLICATIONS

Machine translation of DE20021405, Feb. 15, 2001, provided with Applicants' Jul. 25, 2014 IDS.*

(Continued)

*Primary Examiner* — Daniel S Larkin
(74) *Attorney, Agent, or Firm* — Senniger Powers LLP

(57) ABSTRACT

A single-use coring probe for collecting a frozen aliquot from a frozen biological sample includes a hollow coring bit and an ejector adapted. The ejector is operable to eject a frozen sample core from the bit as it moves from a retracted position to an extended position. Use of the ejector converts the probe to a disabled configuration to discourage reuse of the coring probe to obtain another sample. The probe may include a locking mechanism adapted to prevent re-use of the single-use coring probe by locking the ejector in the extended position. A hand-held coring device can be used to take frozen sample cores from frozen samples. A tissue container is suitable for holding a frozen tissue sample in frozen storage and also for holding the sample while the sample is sectioned and/or a full-depth frozen sample core is extracted from the frozen tissue.

13 Claims, 37 Drawing Sheets

(56) References Cited

U.S. PATENT DOCUMENTS

| | | |
|---|---|---|
| 6,951,761 B2 | 10/2005 | Star et al. |
| 7,070,950 B2 | 7/2006 | Song et al. |
| 7,611,473 B2 | 11/2009 | Boock et al. |
| 8,197,837 B2 | 6/2012 | Jamiolkowski et al. |
| 8,278,034 B2 | 10/2012 | Muraca |
| 2002/0129975 A1 | 9/2002 | Barta |
| 2002/0168639 A1 | 11/2002 | Muraca |
| 2003/0082797 A1* | 5/2003 | Rastorgoueff ..... A61B 10/0266 435/309.1 |
| 2005/0234336 A1 | 10/2005 | Beckman et al. |
| 2005/0282246 A1 | 12/2005 | Postoyalko et al. |
| 2006/0099114 A1* | 5/2006 | Caldwell .............. B26D 7/1818 422/503 |
| 2006/0199169 A1 | 9/2006 | Lam et al. |
| 2007/0166834 A1 | 7/2007 | Williamson, IV et al. |
| 2008/0103411 A1* | 5/2008 | Van Bladel ........ A61B 10/0266 600/564 |
| 2008/0227662 A1 | 9/2008 | Stromberg et al. |
| 2009/0286326 A1* | 11/2009 | Caldwell .......... G01N 27/44704 436/174 |
| 2010/0184126 A1* | 7/2010 | Rutty ...................... G01N 1/04 435/40.5 |
| 2011/0179888 A1* | 7/2011 | Danesh .................... G01N 1/08 73/864.44 |
| 2013/0323715 A1* | 12/2013 | Smith ..................... B01L 3/508 435/4 |
| 2014/0335554 A1* | 11/2014 | Larson ..................... G01N 1/08 435/29 |

FOREIGN PATENT DOCUMENTS

| | | |
|---|---|---|
| EP | 2249140 A1 | 11/2010 |
| WO | WO 0104599 A1 * | 1/2001 ............... G01N 1/08 |
| WO | 2007084483 A2 | 7/2007 |
| WO | 2007095366 A2 | 8/2007 |
| WO | 2012074771 A2 | 6/2012 |
| WO | 0198525 A2 | 12/2012 |

OTHER PUBLICATIONS

The National Bioethics Advisory Commission, "Ethical Issues in Human Stem Cell Research; vol. I, Report and Recommendations of the National Bioethics Advisory Commission", Sep. 1999, Rockville, Maryland, 121 pgs.

International Search Report and Written Opinion for PCT/US2013/051902, dated Apr. 25, 2014, 20 pages, Rijswijk, The Netherlands.

Australian Patent Examination Report No. 1, Date of Issue: Nov. 2, 2016, Patent Application No. 2013295813, (3) pgs.

* cited by examiner ns of frozen storage space, labor, and larger inventory of sample con-
APPARATUS AND METHODS FOR ALIQUOTTING FROZEN SAMPLES

CROSS-REFERENCE TO RELATED APPLICATION

This application is a non-provisional patent application based on U.S. Provisional Application Ser. No. 61/784,753, filed Mar. 14, 2013, and U.S. Provisional Application No. 61/675,016, filed Jul. 24, 2012, the entire contents of which are each incorporated by reference.

FIELD OF INVENTION

The present invention relates generally to apparatus and methods for taking frozen aliquots from a frozen biological sample while maintaining integrity of the samples, and more particularly to apparatus and methods for ensuring a frozen aliquot taken from a frozen sample is suitable material for analysis.

BACKGROUND

Biological samples are commonly preserved to support a broad variety of biomedical and biological research that includes but is not limited to translational research, molecular medicine, and biomarker discovery. Biological samples include any samples which are of animal (including human), plant, protozoal, fungal, bacterial, viral, or other biological origin. For example, biological samples include, but are not limited to, organisms and/or biological fluids isolated from or excreted by an organism such as plasma, serum, urine, whole blood, cord blood, other blood-based derivatives, cerebral spinal fluid, mucus (from respiratory tract, cervical), ascites, saliva, amniotic fluid, seminal fluid, tears, sweat, any fluids from plants (including sap); cells (e.g., animal, plant, protozoal, fungal, or bacterial cells, including buffy coat cells; cell lysates, homogenates, or suspensions; microsomes; cellular organelles (e.g., mitochondria); nucleic acids (e.g., RNA, DNA), including chromosomal DNA, mitochondrial DNA, and plasmids (e.g., seed plasmids); small molecule compounds in suspension or solution (e.g. small molecule compounds in DMSO); and other fluid-based biological samples. Biological samples may also include plants, portions of plants (e.g., seeds) and tissues (e.g., muscle, fat, skin, etc.), including healthy tissue and diseased tissue (e.g., tumors).

Biobanks typically store these valuable samples in containers (e.g., tubes, vials, or the like) and cryopreserve them (e.g., in freezers at −80 degrees centigrade, or lower using liquid Nitrogen or the vapor phase above liquid Nitrogen) to preserve the biochemical composition and integrity of the frozen sample as close as possible to the in vivo state to facilitate accurate, reproducible analyses of the samples.

From time to time, it may be desirable to run one or more tests on a sample that has been frozen. For example, a researcher may want to perform tests on a set of samples having certain characteristics. A particular sample may contain enough material to support a number of different tests. In order to conserve resources, smaller samples known as aliquots are commonly taken from larger cryopreserved samples (which are sometimes referred to as parent samples) for use in one or more tests so the remainder of the parent sample will be available for one or more different future tests.

Biobanks have adopted different ways to address this need to provide sample aliquots. One option is to freeze a sample in large volume, thaw it when aliquots are requested and then refreeze any remainder of the parent sample for storage in the cryopreserved state until future aliquots are needed. This option makes efficient use of frozen storage space; yet this efficiency comes at the cost of sample quality. Exposing a sample repeatedly to freeze/thaw cycles can degrade the sample's critical biological molecules (e.g., RNA) and damage biomarkers, either of which could compromise the results of any study using data obtained from the damaged samples.

Another option is to freeze a sample in large volume, thaw it when an aliquot is requested, subdivide the remainder of the parent sample in small volumes to make additional aliquots for future tests and then refreeze these smaller volume aliquots to cryopreserve each aliquot separately until needed for a future test. This approach limits the number of freeze/thaw cycles to which a sample is exposed, but there is added expense associated with the larger volume of frozen storage space, labor, and larger inventory of sample containers (e.g. tubes, vials, or the like) required to maintain the cryopreserved aliquots. Moreover, the aliquots can be degraded or damaged by even a limited number freeze/thaw cycles.

Yet another approach is to divide a large volume sample into smaller volume aliquots before freezing them for the first time. This approach can limit the number of freeze thaw cycles to which a sample may be subjected to only one; yet, there are disadvantages associated with the costs of labor, frozen storage space, and sample container inventory requirements with this approach.

When aliquotting using any of the above approaches, the sampling devices used to make the aliquots must be thoroughly cleaned before being used again on another sample. In some cases all traces of the sample may not be removed during the cleaning process (e.g., due to human error, such as failure to supply a cleaning station with the proper cleaning fluids or the like). Contamination of the samples can negatively affect the viability and integrity of a sample. In other cases, a user may wish to use a new sampling device for every sample when a high level of cleanliness is required. For example, some applications (e.g., cell-based material research, forensic analysis, etc.) require use of equipment that is substantially free from nucleotides, nucleic acids (e.g., DNA and RNA), nucleases (e.g., DNase and RNase), and any other enzymes or biological molecules that can degrade or contaminate the biological sample. Other applications may require sterile working conditions or equipment. Although it is possible to clean a sampling device sufficiently to achieve these high levels of cleanliness as part of a reliable workflow, some users may feel more confident if the sampling device is not re-used.

U.S. Pat. No. 8,448,456, the contents of which are hereby incorporated by reference, discloses a system for extracting frozen sample cores from a frozen biological sample without thawing the original (parent) sample. The system uses a drill including a hollow coring bit to take frozen core samples from the original parent samples without thawing the parent samples. One or more frozen sample cores from a parent sample, depending on the amount of sample needed for a particular test, can constitute the aliquot for the test. After an aliquot is obtained from a parent sample, the remainder of the sample is returned to frozen storage in its original container until another aliquot from the parent sample is needed for a future test.

U.S. application Ser. No. 13/359,301, the contents of which are hereby incorporated by reference, discloses a robotic end effector for collecting frozen aliquots from an array of frozen samples in a plurality of containers. The end effector uses a hollow coring bit to take frozen sample cores from the original samples without thawing the parent samples. A fill-level detection system detects the position of the surfaces of the frozen samples to determine if a sufficient amount of frozen sample cores have been taken from a particular frozen sample to obtain a predetermined amount of material from that frozen sample.

PCT application No. PCT/US2011/61214 and U.S. provisional application No. 61/418,688, the contents of which are hereby incorporated by reference, disclose a method of obtaining an aliquot of a frozen sample using a coring device. The location of the coring is selected to be at a radial position where the concentration of a substance of interest in the frozen sample core is representative of the overall concentration of the substance in the parent sample.

U.S. Provisional Application No. 61/640,662 and U.S. application Ser. No. 13/489,234, the contents of which are hereby incorporated by reference, disclose a machine vision system for use with a system for obtaining frozen sample cores. The machine vision system includes a camera and a processor that receives image data from the camera to determine locations where frozen sample cores have already been taken from a frozen biological sample.

In pathology and biomedical research, tissue samples are often stored and sampled. Conventionally, the tissue samples were subjected to formalin fixation and embedded in paraffin or optimal cutting temperature compound (OCT). The embedded tissue is fixed to a slide sectioning device, such as a microtome or cryotome, and a thin section of the tissue is sliced off the top of the sample. The thin section is evaluated on a slide, and the area of interest of the sample (e.g., tumor) is identified (e.g., using a marking device to circle the area of interest). The slide is then lined up with the remainder of the tissue sample to determine where the area of interest is on the remaining tissue. The tissue sample is then moved to a processing or sampling area or device, and a sample is taken from the area of interest, typically by using a scalpel to cut the sample into pieces and extract a portion of tissue from the area of interest. One problem with formalin fixed embedded tissue is that biomarkers degrade and the research quality of the tissue is negatively affected by the fixation process. Thus, the use of frozen tissue is desirable over fixed material. However, the frozen tissue samples are typically stored in a variety of containers and processed with methods that require thawing of the samples to obtain portions of tissue from the areas of interest. The frozen tissue samples must still be sectioned for a slide and then moved to a sampling device. The variety of containers used to store a tissue sample, as well as the multiple apparatuses and fixtures that are needed to determine the area of interest and to sample a tissue sample, complicate the process.

The present inventors have developed systems and methods, which will be described below, that improve the ability to provide frozen aliquots from a frozen biological sample (e.g., frozen fluid and/or frozen tissue samples) using a system that extracts frozen sample cores from frozen biological samples without thawing the original (parent) samples. Furthermore, the present inventors have developed systems and methods to reduce the complexity of frozen tissue sample sampling and create a uniform process by mounting the frozen tissue sample in a tissue sample container that can be used with a slide sectioning device and with a frozen tissue sampling device.

SUMMARY

One aspect of the invention is a single-use coring probe for collecting a frozen aliquot from a frozen biological sample. The single-use coring probe includes a hollow coring bit for taking a frozen sample core from the frozen biological sample. An ejector is adapted to eject the frozen sample core taken by the hollow coring bit from the hollow coring bit. The ejector is moveable from a retracted position to an extended position and is operable to push a frozen sample core out of the coring bit as it moves from the retracted position to the extended position. A locking mechanism is adapted to prevent re-use of the single-use coring probe.

Another aspect of the invention is a coring probe for collecting a frozen aliquot from a frozen biological sample. The coring probe includes a hollow coring bit for taking a frozen sample core from the frozen biological sample. An ejector is adapted to eject the frozen sample core taken by the hollow coring bit from the hollow coring bit. The ejector is moveable from a retracted position to an extended position and operable to push a frozen sample core out of the coring bit as it moves from the retracted position to the extended position. A coupling is adapted to releasably connect the hollow coring bit to a coring device. The coupling is affixed to the coring bit and is adapted to remain affixed to the coring bit after disconnection of the coring bit from the coring device.

Still another aspect of the invention is a method of taking a frozen sample core from a frozen sample. The method includes inserting a coring bit into the frozen sample to obtain the frozen sample core. An ejector is moved from a retracted position to an extended position to eject the frozen sample core from the coring bit. The coring bit is disabled to discourage reuse of the coring bit.

In another method of taking a frozen sample core from a frozen sample, a hollow coring bit is inserted into the frozen sample to obtain the frozen sample core. An ejector is moved from a retracted position to an extended position to eject the frozen sample core from the coring bit. The ejector is locked in the extended position to discourage reuse of the coring bit.

Another aspect of the invention is a handheld coring device for collecting frozen aliquots from frozen biological samples. The handheld coring device includes aa motor and a single-use coring probe connected to the motor such that rotational movement and torque from the motor is transmitted to the single-use coring probe. The single-use coring probe is configured to discourage re-use of the single-use coring probe after it has been used to collect a frozen sample core from a frozen biological sample. The single-use coring probe is selectively detachable from the motor.

Still another aspect of the invention is a tray suitable for use with a hand-held coring device for taking frozen sample cores from frozen biological samples.

Yet another aspect of the invention is a single-use coring probe for taking a frozen sample core from a frozen biological sample by insertion of the single-use coring probe into the frozen biological sample followed by withdrawal of the single-use coring probe from the frozen biological sample. The single-use coring probe is configured to discourage re-use of the single-use coring probe after it has been used to collect a frozen sample core from a frozen biological sample.

Still another aspect of the invention is a single-use coring probe adapted for taking a frozen sample core from a frozen biological sample by insertion of the single-use coring probe into the frozen biological sample followed by withdrawal of the single-use coring probe from the frozen biological sample. The single-use coring probe includes a mechanism that disables the single use coring probe after a single use so the single-use coring probe is no longer suitable for taking another frozen sample core from a frozen biological sample after said single use.

In another aspect of the invention a single-use coring probe for taking a frozen sample core from a frozen biological sample by insertion of the single-use coring probe into the frozen biological sample followed by withdrawal of the single-use coring probe from the frozen biological sample is adapted so use of the single-use coring probe to take a single frozen sample core automatically disables the single-use coring probe.

Another aspect of the invention is a method of increasing the likelihood that an operator uses only coring probes that are free from nucleotides, nucleic acids, and nucleases to obtain a plurality of frozen sample cores from a plurality of different frozen biological samples. The method includes providing the operator with a plurality of coring probes that are free from nucleotides, nucleic acids, and nucleases that are configured so use of each coring probe to extract a single frozen sample core converts the respective coring probe to a disabled configuration in which the coring probes are inoperable to extract frozen sample cores from any frozen biological samples.

Yet another aspect of the invention is a system for collecting frozen aliquots from frozen biological samples contained in frozen sample containers. The system includes a handheld coring device having a motor and a coring probe connected to the motor such that rotational movement and torque from the motor is transmitted to the coring probe. The system also includes a positioning guide adapted to be positioned atop the frozen sample containers. The positioning guide has an opening extending therethrough adapted to guide the coring probe into the frozen sample container.

Another aspect of the invention is a tissue sample container for use holding a frozen tissue sample. The container has a base having a height and a lid. The lid is selectively engageable with the base for enclosing a tissue sample fixed to the base within the container while the tissue sample is preserved in frozen storage. The lid has a height greater than the height of the base. The container includes a coupling on the base adapted to mount the base to a slide sectioning device so the tissue sample can be sectioned while it is fixed to the base.

Still another aspect of the invention is a kit for preparing a tissue sample for frozen storage. The kit includes a container. The container includes a base having a height and a lid having a height greater than the height of the base. The lid is selectively moveable relative to the base to cover and uncover a tissue sample received in the base. The kit also includes a sacrificial material that can be placed in the base to support a tissue sample at a position above a bottom of the base. The kit includes instructions instructing a user to position a tissue sample on the sacrificial material, place the lid on the base to enclose the tissue sample in the container, and place the tissue sample and container in frozen storage.

Yet another aspect of the invention is a method of mounting a tissue sample in a tissue sample container. The method includes placing a layer of sacrificial material in a bottom of the tissue sample container. The tissue sample is placed on a top surface of the sacrificial material such that the tissue sample is supported by the sacrificial material at a position above the bottom of the container. The tissue sample is frozen in the container.

Another aspect of the invention is a method of preparing and sampling a tissue sample in a tissue sample container. The method includes mounting the tissue sample in the tissue sample container. The tissue sample container and tissue sample are stored in frozen storage. A frozen sample core is extracted from the frozen tissue sample while the sample remains in the tissue sample container.

Yet another aspect of the invention is a system for storing frozen tissue samples. The system includes a container including a base and a lid selectively engageable with the base for opening and closing the container. The system includes a tissue carriage sized and shaped to be enclosed within the container. The tissue carriage has a support surface for supporting a sample of frozen tissue.

Still another aspect of the invention is a tissue carriage for supporting a frozen tissue sample on a cryotome while the cryotome is used to section the frozen tissue sample. The tissue carriage has a support surface for supporting the frozen tissue sample and a peripheral sidewall extending up from a perimeter of the support surface. The tissue carriage has a coupling adapted to connect the tissue carriage to the cryotome and hold the support surface stationary while the cryotome is used to section the frozen tissue sample.

Another aspect of the invention is a tissue carriage for supporting a frozen tissue sample on a cryotome while the cryotome is used to section the frozen tissue sample. The tissue carriage has a support surface for supporting the frozen tissue sample and a peripheral sidewall extending up from a perimeter of the support surface. The tissue carriage has a lower surface opposite the support surface. The lower surface has a rib thereon positioned to stiffen the support surface.

Yet another aspect of the invention is a method of storing a tissue sample. The method includes affixing the tissue to a tissue carriage. The tissue is enclosed in a container. The container is placed the container into frozen storage while the tissue is contained within the container.

Other objects and features will in part be apparent and in part pointed out hereinafter.

BRIEF DESCRIPTION OF THE DRAWINGS

Corresponding reference numbers indicate corresponding parts throughout the drawings.

DETAILED DESCRIPTION

Figure 1:
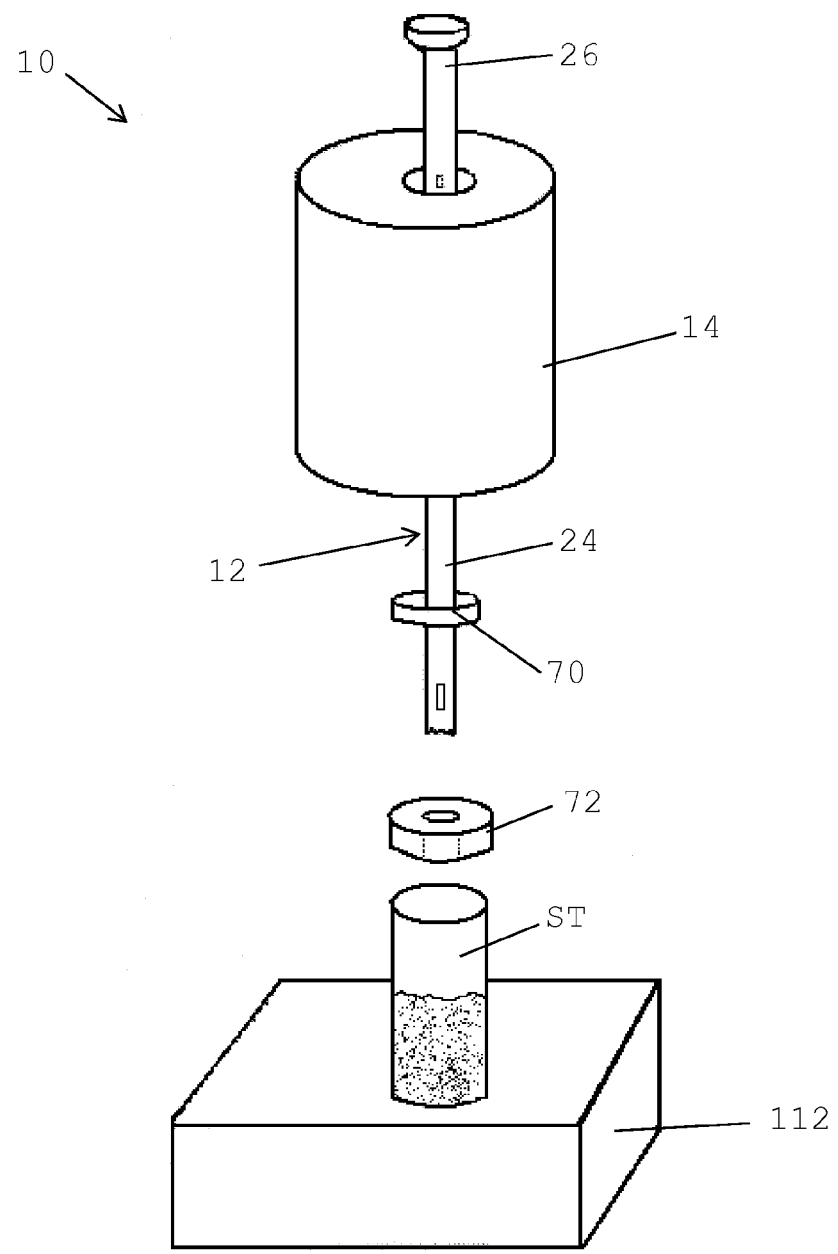
FIG. 1 is a schematic perspective of one embodiment of a hand-held system for taking frozen aliquots from a frozen biological sample.
Figure 2:
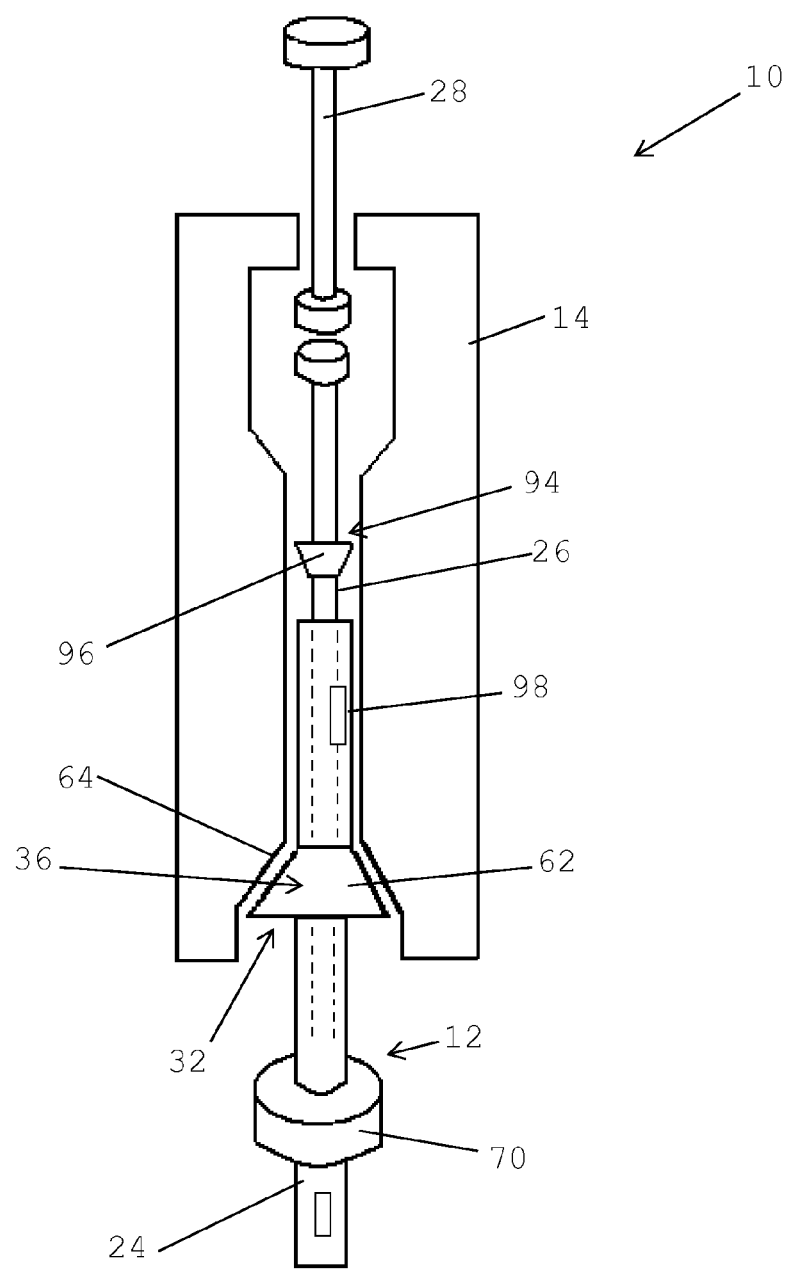
FIG. 2 is a front elevation in partial section of a handheld coring device including a single-use coring probe for taking frozen aliquots from a frozen biological sample.

A handheld coring device for extracting frozen sample cores from frozen samples (e.g., a cryopreserved biological sample from a biobank), generally designated 10, is illustrated schematically in FIGS. 1 and 2. The handheld coring device 10 includes a coring probe 12 and a drive motor 14 adapted to rotate the coring probe as a user extends the rotating coring probe into a frozen sample, such as a frozen sample contained in a container ST as illustrated in FIG. 1. The container ST can be supported in a tray 112, as described in more detail below. However, the container ST can be supported in other ways within the scope of the invention. The drive motor 14 is suitably a variable speed drive motor that permits the speed at which the coring probe 12 is rotated to be selectively adjusted according to the desired operating parameters for the particular frozen biological sample being aliquotted.

Suitably, the coring probe 12 is a disposable coring probe configured for only a single use. Use of a single-use coring probe prevents the risk of cross-contamination of samples (e.g., due to improper cleaning of the probe between samples) and eliminates the need for a cleaning process. The single-use coring probe 12 is suitable for use with the handheld coring device 10 to collect a frozen aliquot from a frozen biological sample in a frozen sample container ST. However, the single-use coring probe 12 can be adapted for use with any coring device, such as automatic or robotic coring devices, within the broad scope of the invention. Suitably, the single-use coring probe 12 is free from nucleotides, nucleic acids (e.g., DNA and RNA), nucleases (e.g., DNase and RNase), and any other enzymes or biological molecules that can degrade or contaminate a biological sample. The single-use coring probe 12 can also be sterile. The single-use coring probe 12 can be packaged to maintain the sterile or nucleotide-free, nucleic acid-free, nuclease-free, enzyme-free, or biological marker-free condition of the single-use coring probe until the package is opened for use with the handheld coring device 10 or other apparatus for taking frozen sample cores.

The single-use coring probe 12 increases the likelihood that a user will use only probes that are free from nucleotides, nucleic acids (e.g., DNA and RNA), nucleases (e.g., DNase and RNase), and any other enzymes or biological molecules that can degrade or contaminate a biological sample by discouraging reuse of the coring probe. Likewise, if the single-use coring probe 12 is sterile, it increases the likelihood that a user will only use probes that are sterile. Upon use of a single-use coring probe 12 to extract a frozen sample core from a frozen biological sample, the probe is no longer free from nucleotides, nucleic acids, nucleases, and other enzymes or biological molecules that can degrade or contaminate a biological sample. Similarly, if the single-use coring probe 12 is sterile before use, it is no longer sterile after use. Thus, after the single-use coring probe 12 has been used to extract a frozen sample core from a frozen biological sample, the probe is disabled so as to be inoperable to extract another frozen sample core.

Although it may be possible in some cases to restore operability to a single-use coring probe after use, the coring probe 12 is suitably adapted to ensure that the effort required to do so makes it impractical to restore operability and reuse the coring probe. Thus, the practical effect is that a user must use a new single-use coring probe 12 (e.g., a probe that is free from nucleotides, nucleic acids, nucleases, and other enzymes or biological molecules that can degrade or contaminate a biological sample and/or that is sterile) for use in obtaining another frozen sample core. It is also understood that a relatively small deterrent to reuse of a coring probe can effectively prevent reuse of coring probes because there is little incentive to bypass a coring probe replacement step in a protocol specifying probes are not to be reused when it is more convenient to follow the protocol and replace the used coring bits than it is to restore operability to a single-use coring bit that has already been used.

Figure 3:
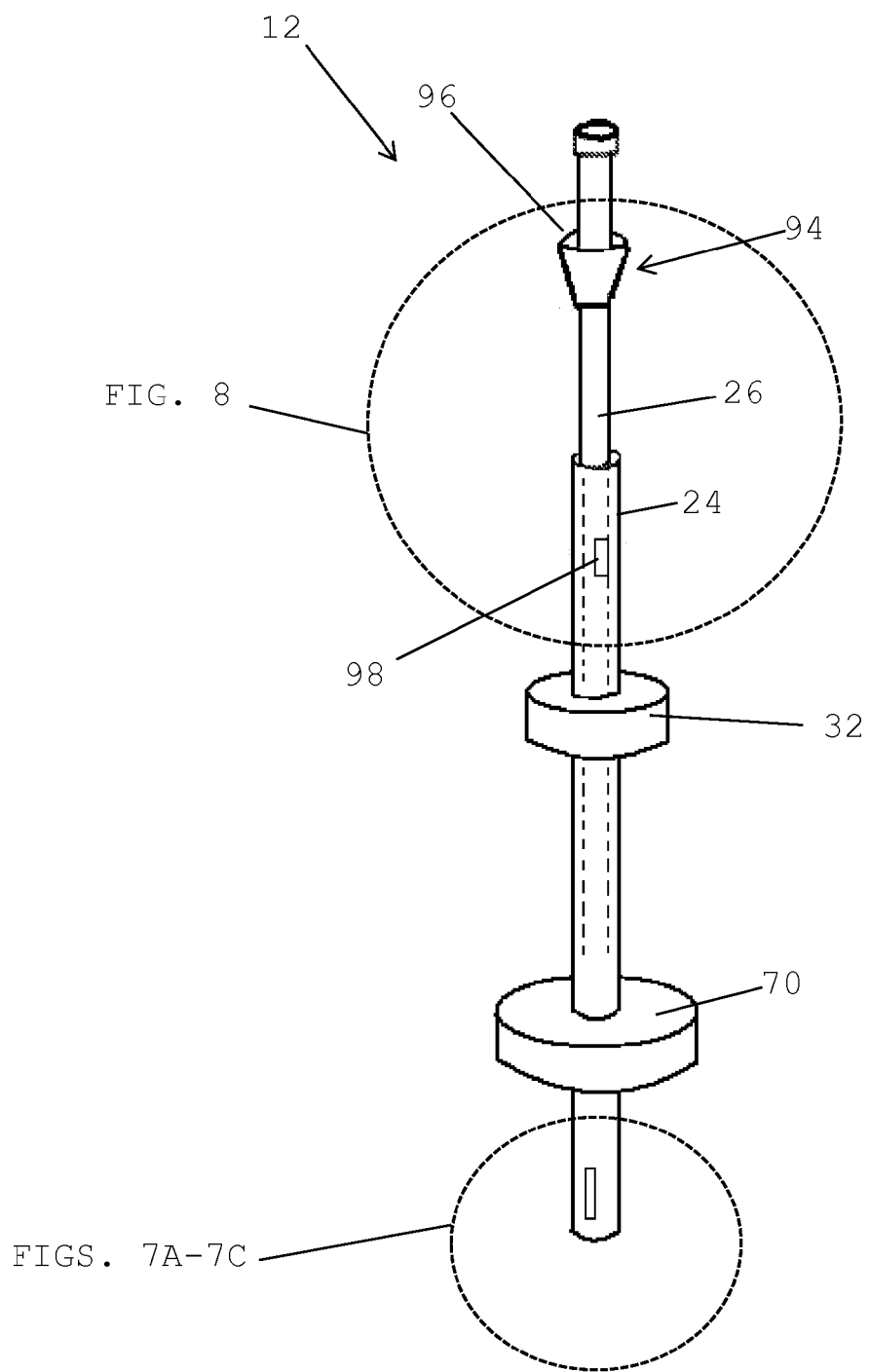
FIG. 3 is a front elevation of one embodiment of a single-use coring probe.

As illustrated schematically in FIGS. 2 and 3, one embodiment of a single-use coring probe 12 includes a hollow coring bit 24 (e.g., hollow needle having a cutting tip) and an ejector 26 adapted to eject a frozen sample core contained in the coring bit 24 from the end of the coring bit. The coring bit 24 and/or ejector 26 can be manufactured by injection molding, extrusion, casting, machining or grinding, combinations thereof, or other techniques. Further the coring bit 24 and/or ejector 26 can be assembled from multiple components that are joined (e.g., glued, fastened, welded, etc.) to one another to make the finished piece, either with all the components being made of the same material or with different components being made from different materials. The coring bit 24 and/or ejector 26 can also each be formed as one integral piece within the scope of the invention.

The materials selected for the coring bit 24 suitably exhibit one or more of the following characteristics: resistance to torsional stresses in the case of system that uses a rotary drilling action and/or resistance to impact forces in the case of system that uses a reciprocating linear drilling action, ability to maintain a cutting edge, and does not become too brittle at subfreezing temperatures (e.g., at no more than −10 degrees C., more suitably no more than −40 degrees C., still more suitably no more than −60 degrees C., and still more suitably at about −80 degrees C.). The materials for the ejector 26 can in some cases be lower cost materials than the materials for the coring bit 24. For example, the ejector 26 is not normally subjected to the same level of torsional stress or impact force as the coring bit. Also, the ejector 26 is not normally required to perform any cutting action so it is not important for the material used in the ejector to be able to maintain a cutting edge. The material is desirably relatively strong and exhibits good toughness at low temperatures. The material for the coring bit 24 and ejector 26 can be made of natural materials that exhibit the desired characteristics or the material may be modified to change its characteristics to make the material suitable for use in the coring bit 24 and/or ejector 26.

A non-limiting list of suitable materials for the coring bit 24 includes Stainless Steel (e.g., 303, 304, or 316 varieties), Titanium, Inconel 625, Polyethermide (e.g., Ultem®), Polycarbonate (e.g., Lexan®, Hyzod®, Cyrolon®, or Staticon®) Acrylic (e.g., Acrylite®, Plexiglas®, Lucite®, Staticon®), Acrylic-PVC Alloys, Acrylonitrile-Butadiene-Styrene (ABS) (e.g., Cycolac®), Polyolefins (e.g., Polyethylenes & Polypropylene, such as UHMW® & Polyslick® 502), polyurethane (e.g., Versathane®, or Isoplast®); High Impact Polystyrene (HIPS), nylon, glass reinforced nylon, ceramics, glass whisker reinforced ceramics, Polyvinyl Chloride (PVC), Acetal (e.g., Delrin®, Celcon®, or Ensital®), Polyether ether ketone (PEEK) (e.g., VicTrex®), Fluoroplastics-Teflon (Teflon®, Kel-F®, Kynar®, Rulon®, or Tefzel®), Polyethylene, and Aluminum.

A non-limiting list of suitable materials for the ejector includes Stainless Steel (e.g., 303 or 304 varieties), Aluminum, TPE plastics, polypropylene, Polyurethane, Polyvinyl Chloride (PVC); Polyether ether ketone (PEEK) (e.g., VicTrex®), Fluoroplastics-Teflon (Teflon®, Kel-F®, Kynar®, Rulon®, or Tefzel®), nylon, glass reinforced nylon, polystyrene (reinforced and non-reinforced), and Acrylonitrile-Butadiene-Styrene (ABS) (e.g., Cycolac®).

The ejector 26 is movable from a retracted position to an extended position and operable to push any frozen sample core retained in the coring probe 12 out of the coring probe as it moves from the retracted position to the extended position. For example, the distal end of the ejector 26 suitably moves from a position within the hollow coring bit 24 and spaced from a distal end of the coring bit to a position beyond the distal end of the coring bit as the ejector moves to the extended position. The ejector 26 is suitably movable from the retracted position to the extended position by a plunger 28 located on the handheld coring device 10. The user depresses the plunger 28, which engages the ejector 26 and moves the ejector from the retracted position to the extended position, thus ejecting a frozen aliquot contained in the coring probe 12. Suitably, the frozen core is ejected into a cold destination container (e.g., an aliquot-receiving tube), well plate (e.g., a 96 well plate or other well plate), or other structure to ensure the frozen aliquot remains frozen, thereby maintaining the biological integrity of the frozen aliquot. It is recognized that the frozen core can be ejected into a warm container within the scope of the present invention (e.g., if the core is going to be subjected to tests immediately). Suitably, the single-use coring probe can be detached from the handheld coring device 10 by further depression of the plunger 28 after ejection of the frozen aliquot. Other options for detaching the single-use coring probe 12 are within the broad scope of the present invention. For example, a handheld coring device can include a lever or other actuator separate from the plunger 28 for detaching the single-use coring probe.

The single-use coring probe 12 further includes a coring bit engagement member or coupling 32 adapted to connect the probe to the drive motor 14 in the handheld coring device 10. The coring bit coupling 32 is disposed on the coring bit 24 and is adapted for engagement with a drive motor engagement member or coupling 36 to transmit rotation and torque from the drive motor 14 to the coring bit. The couplings 32, 36 are configured for precise relative positioning, and suitably permit quick attachment and detachment of the single-use coring probe 12 and the drive motor 14.

Figure 4A:
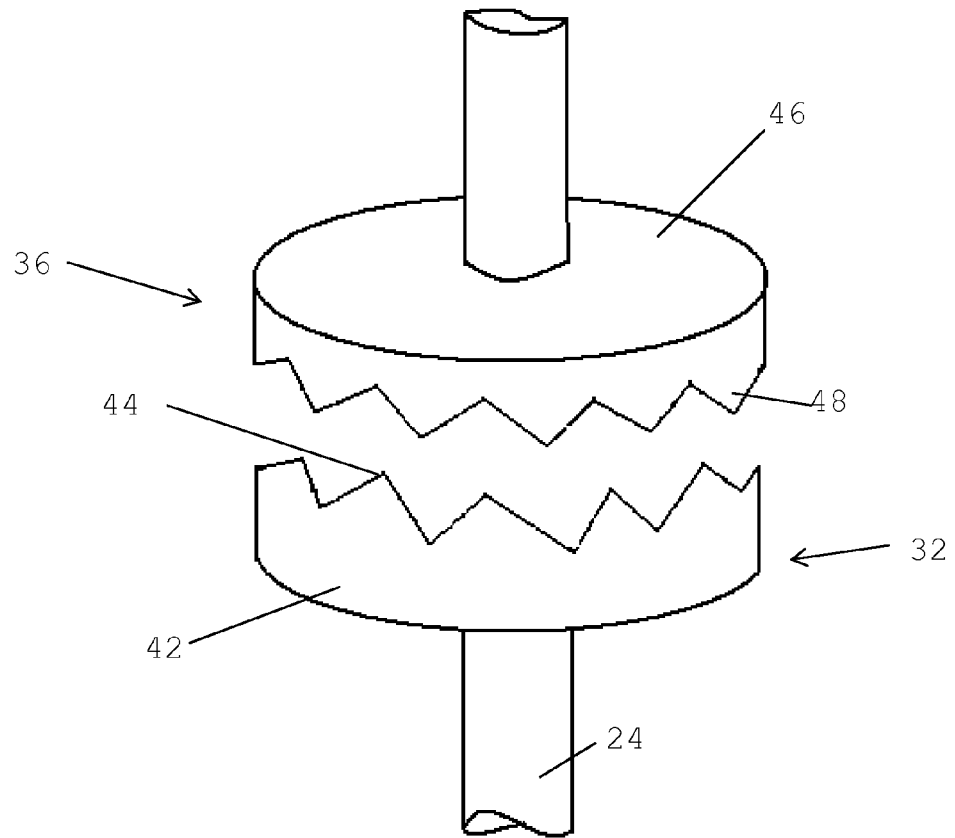
FIG. 4A is schematic of a first embodiment of a coupling between the single-use coring probe and the handheld coring device.

FIGS. 4A-4D illustrate three different examples of couplings that can be used to connect the coring bit 24 to the motor 14. In FIG. 4A, the coring bit coupling 32 includes a flange 42 at the proximal end of the coring bit 24. The flange 42 includes a plurality of teeth 44 formed on a proximal surface of the flange. The motor coupling 36 includes a plate 46 having teeth 48 formed on a distal surface thereof. The plate 46 is connected to the drive shaft of the motor so the motor can rotate the plate. The teeth 44, 48 are configured for engagement with each other, such that rotational movement and torque from the drive motor 14 is translated to the coring bit 24 through the teeth. The flange 42 and the plate 46 can be drawn together into engagement by a magnet, a mechanical lever, or other suitable means (not shown).

Figure 4B:
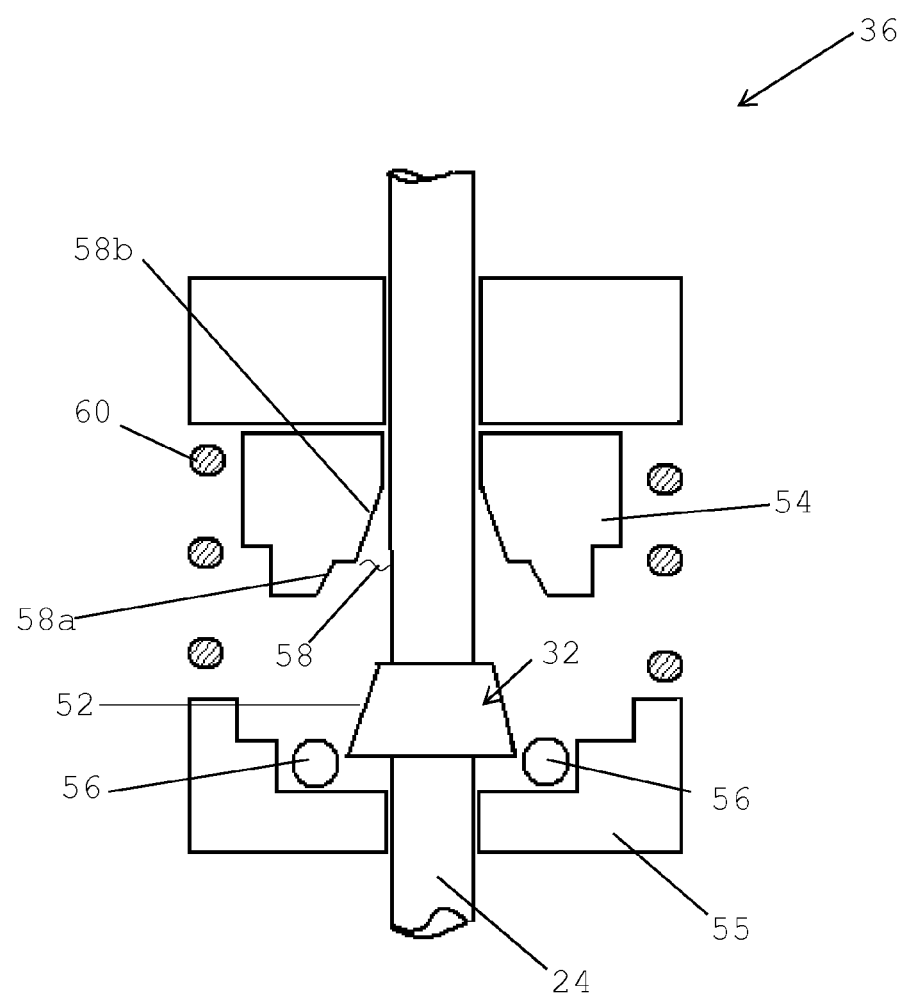
FIG. 4B is a schematic of a second embodiment of a coupling between the single-use coring probe and the handheld coring device, illustrating the coupling in a first position.
Figure 4C:
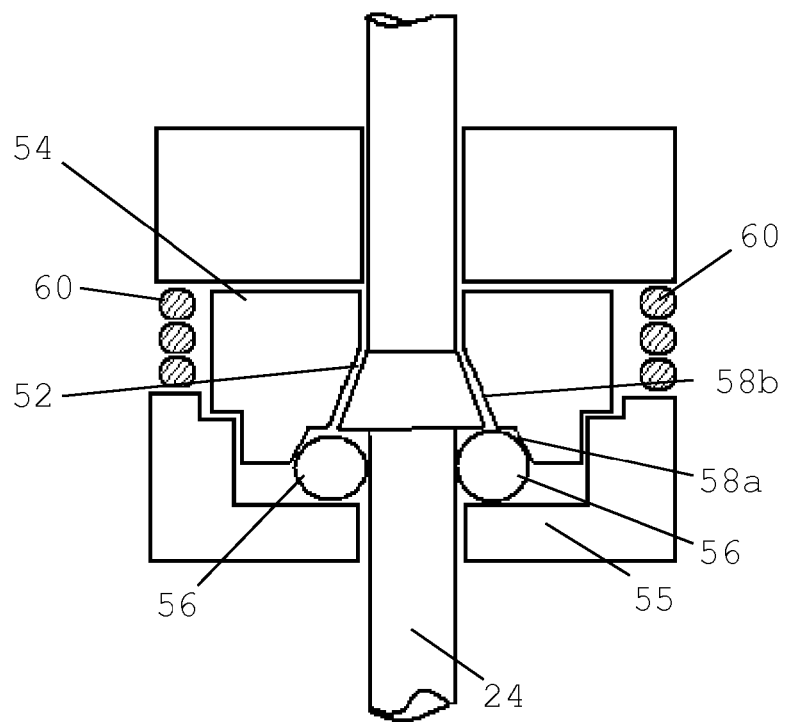
FIG. 4C is a schematic of the second embodiment of FIG. 4B, illustrating the coupling in a second position.

In FIGS. 4B and 4C, the coring bit coupling 32 includes a frusto-conical engagement surface or flange 52 at the proximal end of the coring bit 24. The motor coupling 36 includes a magnet 54, a magnetic ball coupling comprising a magnetic support 55 and a plurality of balls 56 supported in radially-extending tracks (not shown) in the support, an opening 58 defined by the magnet, and a spring 60 or other biasing member positioned to bias the support to move away from the magnet. The balls 56 can be retained in fixed tracks (not shown) that permit movement of the balls radially in and out, but prevent circumferential movement of the balls around the coring probe 12. The opening 58 includes a first tapered portion 58a configured to receive the balls 56 when the balls are at the inward end of their tracks and the support 55 is adjacent the motor magnet 54, and a second tapered portion 58b configured to receive the flange 52 of the coring bit 24. When the support 55 is far enough outside the magnetic field of the magnet 54 that the magnetic attraction between the magnet 54 and magnetic support 55 is weaker than the force of the spring 60, the balls are in a relaxed position and the spring 60 is in an extended position (see FIG. 4B).

To attach the single-use probe 12 to the drive motor 14, the handheld coring device 10 is pressed down over the single-use probe to compress the spring 60 and move the flange 52 into the opening 58. As the spring 60 is compressed (e.g., by the upper surface of a tray or other structure holding the coring probe), the magnetic attraction between the support 55 and the magnet 54 grows stronger and draws the support 55 upward, forcing the balls 56 to move in the fixed tracks upward towards the magnet and inward towards the coring probe 12 (e.g., along a surface of the first tapered portion 58a). The magnetic force between the magnet 54 and the support 55 must be strong enough to overcome the biasing force of the spring 60 when the spring is compressed. When the single-use probe 12 is fully attached to the drive motor 14, the flange 52 is received in the second portion 58b of the opening 58, and the balls 56 are received in the first portion 58a (see FIG. 4C). The balls 56 engage a distal surface of the flange 52 and retain the flange in the opening 58 of the magnet 54, thereby securing the coring probe 12 to the drive motor 14.

The coring probe 12 is released by forcing the support 55 apart from the magnet 54 so that the support is out of the magnetic field of the magnet, thus allowing the spring 60 to bias the support away from the magnet, thereby permitting the balls 56 to fall back into the relaxed position and the single-use coring probe 12 to be removed from the drive motor. The support 55 can be separated from the magnet 54 by actuation of the plunger 28 (e.g., by depressing the plunger further after it has been depressed an initial amount to actuate the ejector 26), or by a separate actuator configured to detach the single-use coring probe 12 from the handheld coring device 10.

Figure 4D:
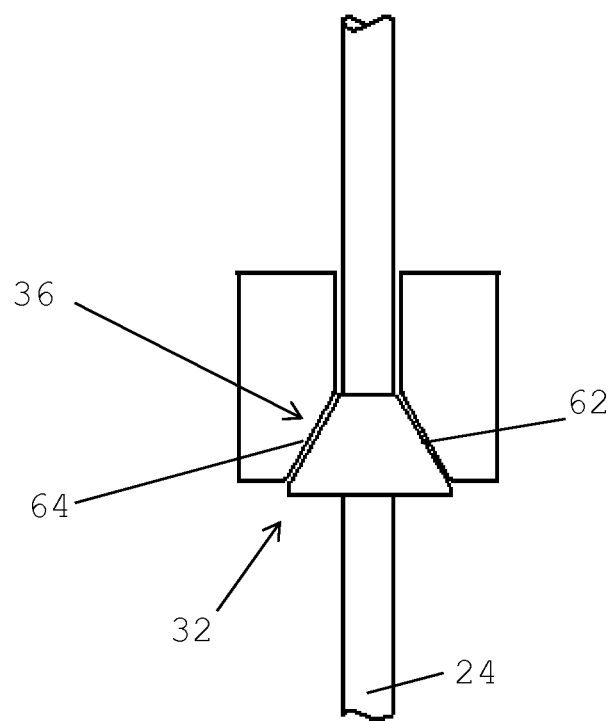
FIG. 4D is a schematic of a third embodiment of a coupling between the single-use coring probe and the handheld coring device.

FIG. 4D illustrates a frictional coupling between the coring probe 12 and the drive motor 14. The coring bit coupling 32 includes a conical flange 62 at the proximal end of the coring bit 24. The motor coupling 36 includes a conical opening 64 adapted to receive the conical flange 62. The couplings 32, 36 can also have interengaging pins or tongue and groove members (not shown) to permit transmission of rotational movement and torque from the motor 14 to the coring bit 24. Other couplings between the motor and the coring probe that transmit rotational movement and torque are within the scope of the present invention.

As seen in FIGS. 2 and 3, the coring probe 12 suitably includes a depth guide 70 extending radially from an outer surface of the coring bit 24. The depth guide 70 is adapted to limit the depth to which the coring bit 24 can be extended into the frozen sample. In particular, the depth guide is suitably positioned so the coring bit 24 can be extended substantially all the way to the bottom of the container but so that the coring bit cannot damage the bottom of the container. Often times, particularly when the sample is a frozen fluid sample, it is desirable to obtain full-depth samples to minimize the effect of vertical concentration gradients on the composition of the frozen sample core, but this is not required within the broad scope of the invention. For example, at least some frozen tissue samples may not develop vertical concentration gradients in the same manner as frozen fluid samples. Also, some tests are designed to detect the presence or absence of particular antibody, compound, or other substance and do not attempt to quantify the amount of such substance in the sample and it is not important to worry about concentration gradients when running these kinds of tests.

Figure 5:
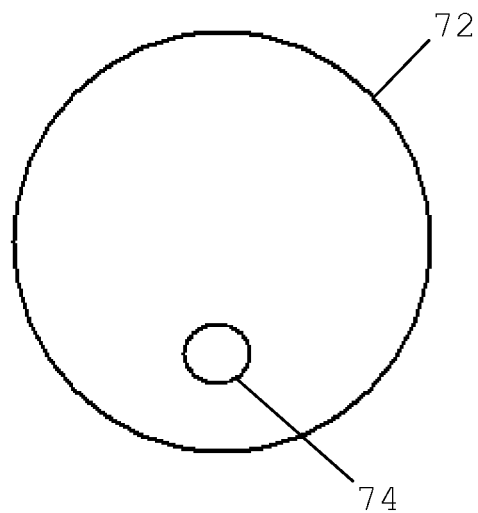
FIG. 5 is top plan of one embodiment of a position guide for use with the handheld coring device.
Figure 6:
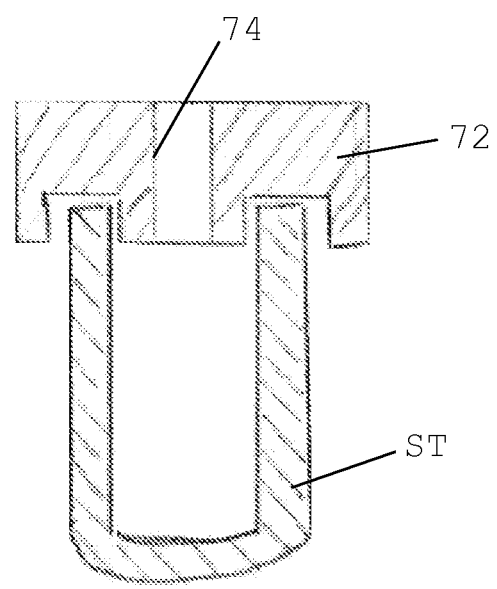
FIG. 6 is a cross section of the position guide positioned atop a container.

In the illustrated embodiment, the depth guide is positioned for use with a position guide 72 positioned atop the frozen sample container (see FIGS. 5 and 6) over the open end of the container. The position guide 72 includes a bore 74 configured to guide the coring bit 24 into the frozen biological sample. The position guide 72 is particularly useful when the single-use coring probe 12 is used with the handheld coring device 10, as the user may unintentionally hold the coring probe in an angled position, rather than the more desirable vertically straight position. The position guide 72 also helps the user obtain the frozen sample core from a predetermined radial position within the container, which can help obtain a sample that has a composition representative of the overall sample composition notwithstanding any radial concentration gradients that may develop during freezing. For example, the bore 74 is suitably positioned so it is offset from the geometric center of the container when the position guide 72 is place atop the container. The bore 74 is closely sized to the diameter of the coring bit 24, such that the coring bit can rotate within the bore while it is still precisely guided to a desired coring position in the frozen sample tube ST. The position guide 72 can have more than one bore 74 within the scope of the present invention.

The position guide 72 acts as a physical stop to set the proper coring depth of the coring bit in the frozen sample container. When the appropriate coring depth has been reached, the depth guide 70 contacts the position guide 72, thereby preventing further distal movement of the coring probe 12 into the frozen sample container. The coring depth guide 70 and position guide 72 are specific to the type and size of different frozen sample containers, trays, and tubes, thus ensuring a desired depth of coring is always achieved. Typically, it is desirable to obtain full-depth samples to minimize the effect of vertical concentration gradients on the composition of the frozen sample core, but this is not required within the broad scope of the invention.

Figure 7A:
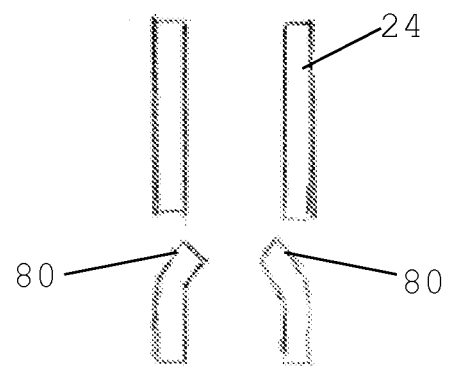
FIG. 7A is a cross section of the distal end of the single-use coring probe, illustrating a first embodiment of a frozen sample core retaining system.
Figure 7B:
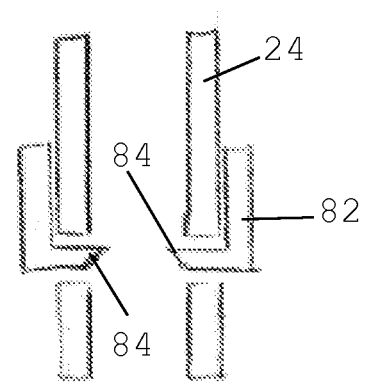
FIG. 7B is a cross section of the distal end of the single-use coring probe, illustrating a second embodiment of a frozen sample core retaining system.
Figure 7C:
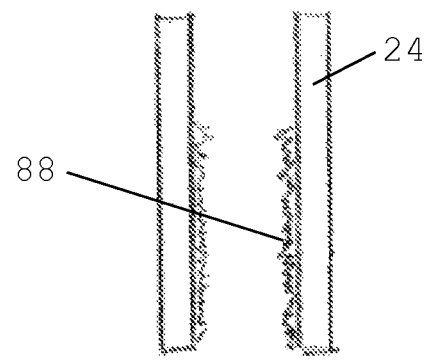
FIG. 7C is a cross section of the distal end of the single-use coring probe, illustrating a third embodiment of a frozen sample core retaining system.

The distal end of the coring bit 24 can suitably include a frozen sample core retaining system to enhance the ability of the coring bit to capture and hold the frozen sample core within the coring probe 12 during the extraction process. The frozen sample core retaining system can include mechanical members or surface treatments to increase the friction and ensure the frozen aliquot is removed from the frozen biological sample with the coring probe 12. Suitably, the frozen sample core retaining system positively holds the frozen sample core in the single-use coring probe 12 until the frozen sample core is ejected from the probe by movement of the ejector 26 to the extended position. FIGS. 7A-7C illustrate example embodiments of the frozen sample core retaining system. It is understood that other frozen sample core retaining systems can be used within the scope of the present invention, or that the frozen sample core retaining system may be omitted within the scope of the present invention.

In FIG. 7A, the frozen sample core retaining system includes at least one tab 80 extending into an interior of the coring bit. The tab(s) 80 can be formed by striking the outer surface of the coring bit 24 with a tool to form the tab and push the severed end of the tab radially inward. The tab(s) 80 are suitably angled so they extend away from the distal end of the coring bit 24 as they extend radially inward to allow the frozen sample core to slide inward past the tab(s) more easily than it can slide past the tab(s) in the outward direction. The tabs 80 engage the frozen aliquot, thereby reducing the likelihood that the frozen aliquot could fall out of the coring bit 24 or remain attached to the frozen biological sample when the probe 12 is removed from the frozen biological sample.

In FIG. 7B, the frozen sample core retaining system comprises a sleeve 82 disposed about a portion of the coring bit 24. The sleeve 82 includes at least one finger 84 extending radially inward at a distal end of the sleeve. In this embodiment, the coring bit 24 includes at least one aperture 86 configured to receive the finger 84 of the sleeve 82. The finger(s) 84 are movable from a first position radially inward to a second position in which the fingers extend through the apertures 86 and into the interior of the coring bit. The fingers 84 can be actuated by moving the sleeve 82 vertically along the coring bit 24, or by any other suitable means. Suitably, the fingers 84 can be biased toward the second position, but maintained in the first position by contact with an external surface of the coring bit 24 until the sleeve 82 is moved vertically to a location that permits the fingers 84 to move to the second position. When the coring bit 24 is coring the frozen biological sample, the fingers 84 remain in the first position external of the coring bit. Once the coring is completed, the fingers 84 are actuated to the second position, thereby engaging the frozen aliquot and ensuring the frozen aliquot remains within the coring probe 12 when the probe is removed from the frozen biological sample. To eject the frozen aliquot, the ejector is actuated to overcome the resistance of the fingers 84. There is no need to move the fingers 84 back to their original position because the coring probe 12 is not intended for re-use.

In FIG. 7C, the frozen sample core retaining system includes an interior surface treatment 88 at the distal end of the coring bit 24. The interior surface treatment 88 can be any treatment suitable to increase the friction between the frozen aliquot and the coring bit 24, such as sand blasting or any other process that increases roughness or adhesion between the coring bit and the frozen sample core. The treated inner surface 88 engages the frozen aliquot and ensures the frozen aliquot remains with the coring probe 12 when the probe is removed from the frozen biological sample.

Figure 8:
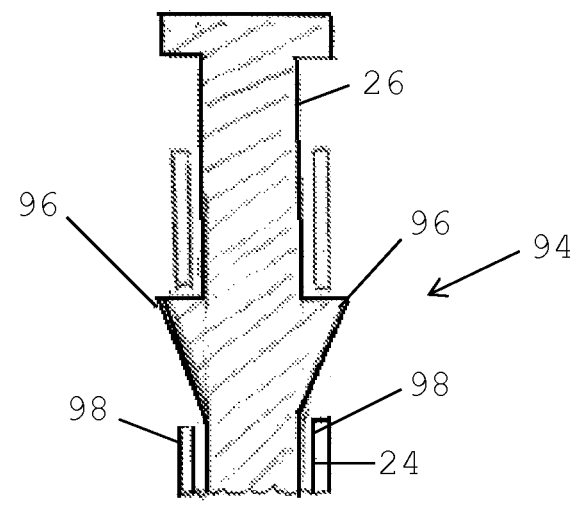
FIG. 8 is a fragmentary cross section showing one embodiment of a locking mechanism at the proximal end of the single-use coring probe.

The single-use probe 12 includes a locking mechanism 94 to ensure that the coring probe is used only once, thereby preventing the possibility for carryover or contamination between samples. The locking mechanism is suitably automatically activated by use of the ejector to eject a frozen sample core from the coring probe. As seen in FIG. 8, the locking mechanism 94 comprises at least one locking barb 96 extending from the exterior surface of the ejector 26 and at least one aperture 98 extending through the exterior surface of the coring bit 24. When the ejector 26 is moved from the retracted position to the extended position to eject the frozen aliquot, each locking barb 96 is received an aperture 98. The locking barb(s) are configured the block retraction of the ejector once they are received in the aperture(s), thereby preventing movement of the ejector from the extended position back to the retracted position. Thus, the ejector is automatically locked in the extended position (e.g., so the ejector 26 extends beyond the distal end of the coring bit 24), which prevents extraction of any additional frozen sample cores.

Figure 9:
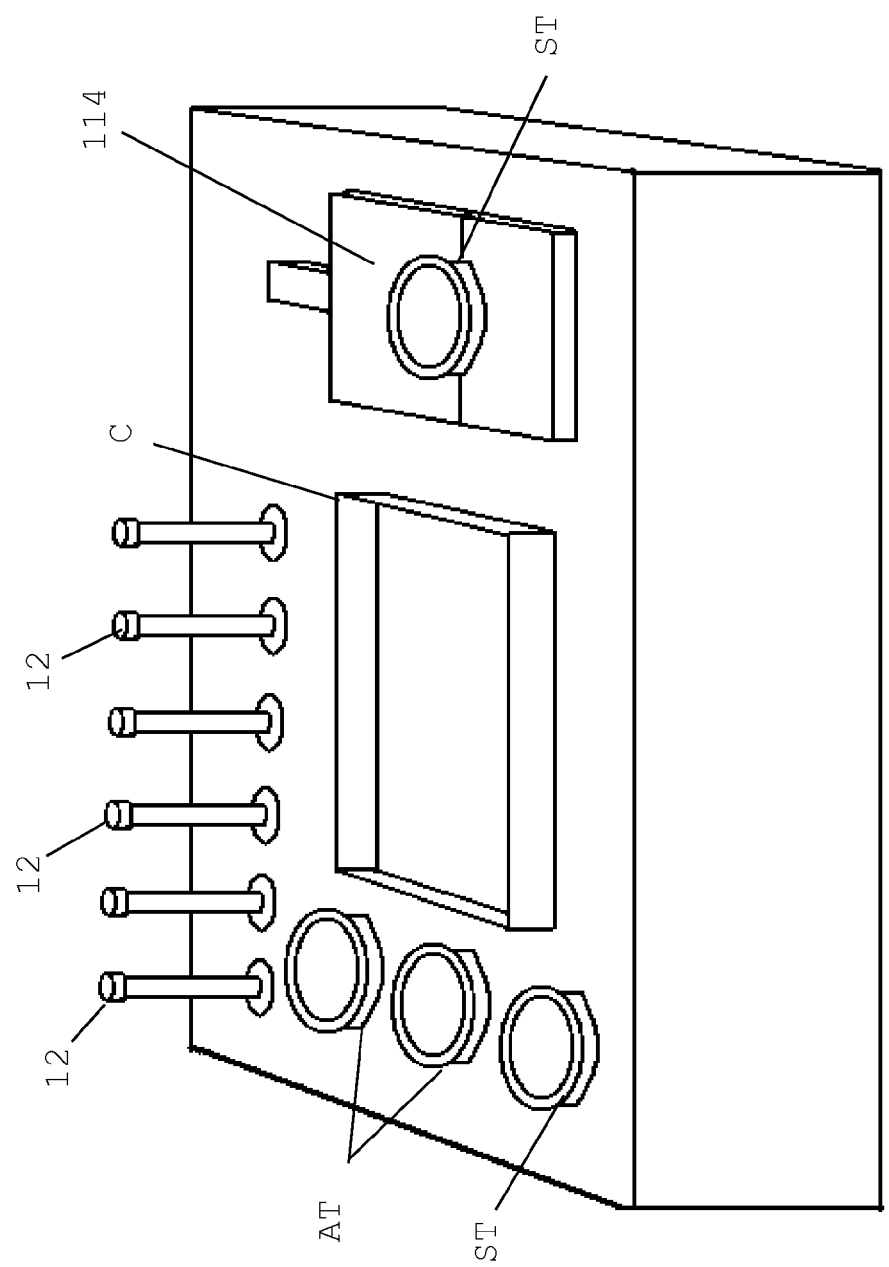
FIG. 9 is a perspective of one embodiment of a tray for use with a handheld coring device.
Figure 10:
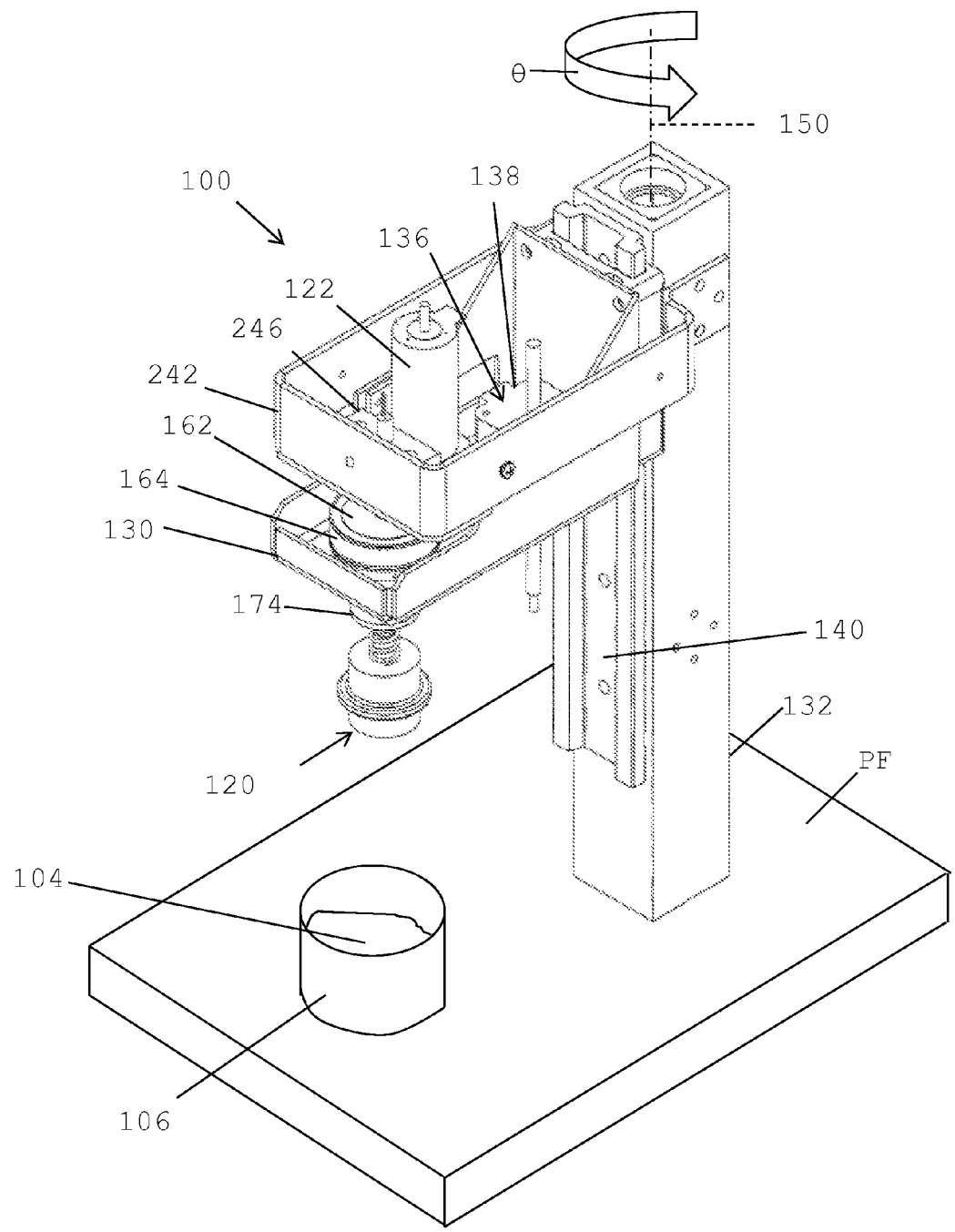
FIG. 10 is perspective of one embodiment of a system for taking frozen sample cores from frozen samples.
Figure 11:
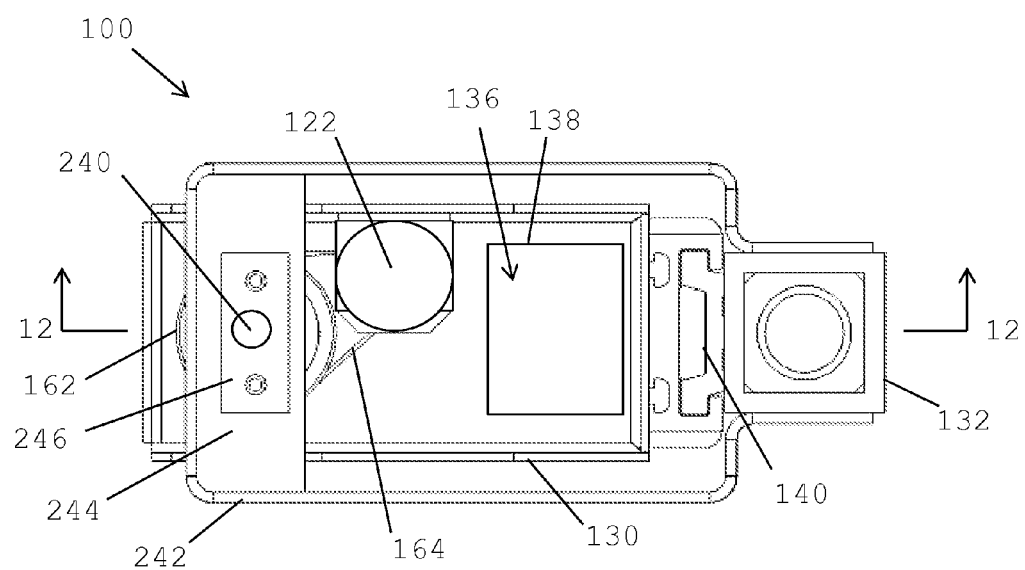
FIG. 11 is top plan of a portion of the system illustrated in FIG. 10.

FIG. 9 illustrates a tray 112 suitable for use with the handheld coring device 10. The tray 112 is configured to keep several pieces of equipment that may be involved in the aliquotting process together and chilled. The tray 112 includes spaces to hold the sample container ST and aliquot-receiving containers AT for receiving frozen sample cores as they are ejected from the coring probe 12. The tray 112 further includes spaces to hold a plurality of single-use coring probes 12, ready for use in the handheld coring device 10. The handheld coring device 10 can be lowered over a single-use coring probe 12 until the motor coupling 36 engages the coring bit coupling 32, thereby securing the single-use probe to the motor 14 and the handheld coring device. Thus, the single-use probe 12 can be attached to the handheld coring device 10 without need for the user to touch the probe, further reducing the possibility of contamination and enhancing safety, as the user need not handle the sharp coring bit. Safety is also enhanced because there is also no need to handle a scalpel as is used in some prior art methods. In case the frozen biological samples are held in a frozen sample container other than a tube, the tray 112 includes a space to hold a larger frozen sample container C. The tray 112 further includes a clamping mechanism 114 for securely holding a frozen sample container or tube for coring. The tray 112 and its contents can be actively or passively frozen to maintain the samples and the probes at a cold temperature. The single-use probes 12 are chilled, suitably to about the same temperature as the frozen sample, to protect the frozen sample from further heating or thawing during the coring and extraction process.

It is also possible to use a single-use coring probe in a non-hand held manual system, semi-automated system or fully-automated system. For example, one example of an automated system for extracting frozen sample cores from frozen samples, generally designated 100, is illustrated in FIGS. 10-18. The system 100 includes a coring bit mount 120 adapted to hold a single-use coring bit 112. The coring bit mount 120 is drivingly connected to a cutting action motor 122 that drives a cutting action of the coring bit 112, as described below. The coring bit mount 120 has an end 124 adapted for releasable connection to the single-use coring bit 112 so the coring bit can be held by the coring bit mount.

The coring bit mount 120, and therefore the single-use coring bit 112 therein, is movable relative to the frozen sample container 106 containing the frozen sample 104. Suitably, the coring bit mount 120 is supported by a carriage 130 that is movable relative to the frozen sample 104. In the illustrated embodiment, the carriage 130 is mounted on a support 132 (e.g., a substantially vertical upright) and is movable relative to the support and the frozen sample 104 by a drive system 136. Suitably, the drive system 136 includes a motor 138, such as a servo motor for precise positioning and movement of the carriage 130. As illustrated in FIGS. 16-21, the carriage 130 is movable along a track 140 on the support 132. The support 132 extends upward from a work area (e.g., a platform PF) for supporting the sample 104 during the coring process. The support 132 is suitably rotatable about a vertical axis 150 as indicated by arrow θ, either manually or under the power of a motor. The drive system 136 is adapted to move the carriage 130 along the track 140 on the support 130 toward and away from the frozen sample 104.

The drive system 136 suitably includes a processor (not shown) configured to control the motor 138. The drive system 136 is suitably configured to receive one or more inputs from a person operating the system 100. For example, the drive system 136 can include a manually-operable actuator or input device (e.g., a button (not shown)) operable by a user to initiate the coring process and produce the relative movement between the carriage 130 and the frozen sample 104. The processor is suitably configured so upon initiation of the coring process, the drive system 136 is operated to move the carriage 130 along the track 140 to insert the coring bit 112 into the sample 104 (e.g., to a pre-determined depth) and operate the motor 122 to drive the cutting action of the coring bit as it is inserted into the sample and then operate the drive system to withdraw the coring bit from the sample. Alternatively, the drive system 136 can be part of a fully-programmable robotic positioning system (e.g., (θ, Z), (θ, r, Z), (x,y,z) Cartesian, etc.) operable to produce the relative movement between the carriage 130 and the frozen sample 104. Other systems and configurations permitting relative movement between the single-use coring bit 112 and the frozen sample 104 are within the scope of the present invention.

The cutting action motor 122 in the illustrated embodiment is drivingly connected to the coring bit mount 120 for driving a cutting action of the coring bit 112 when it is held in the coring bit mount. In the illustrated embodiment, for example, the cutting action motor 122 is suitably adapted to rotate the single-use coring bit 112 as the coring bit is inserted into the frozen sample 104 to take a frozen sample core. Although the cutting action motor 122 in the illustrated embodiment is adapted to drive rotation of the coring bit 112, it is understood that other types of cutting actions are within the scope of the invention. For example, the cutting action motor can be adapted to produce a linear oscillatory cutting action of the single-use coring bit.

Figure 12:
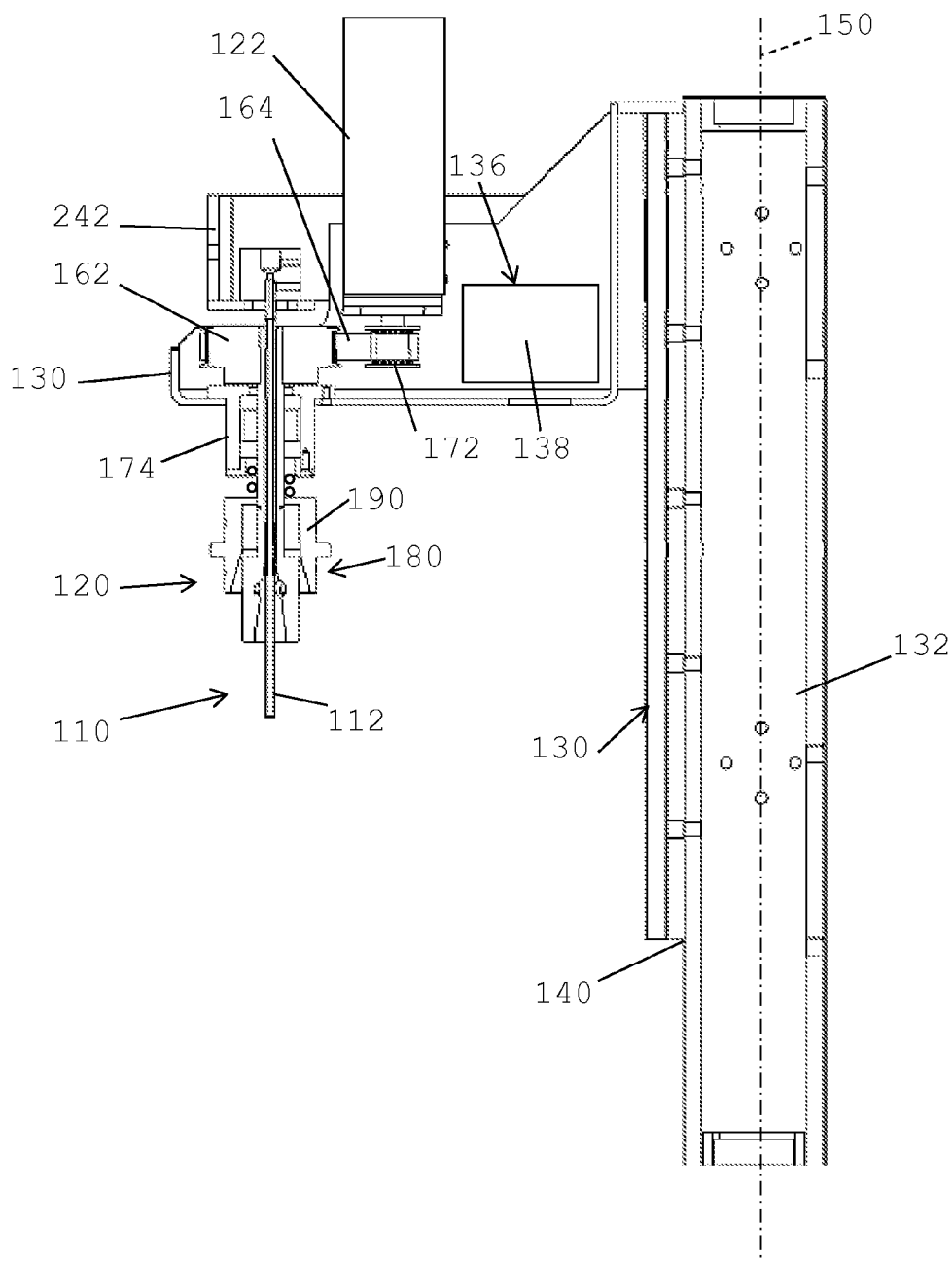
FIG. 12 is a cross section of the system taken in a plane including line 12-12 on FIG. 11.
Figure 15:
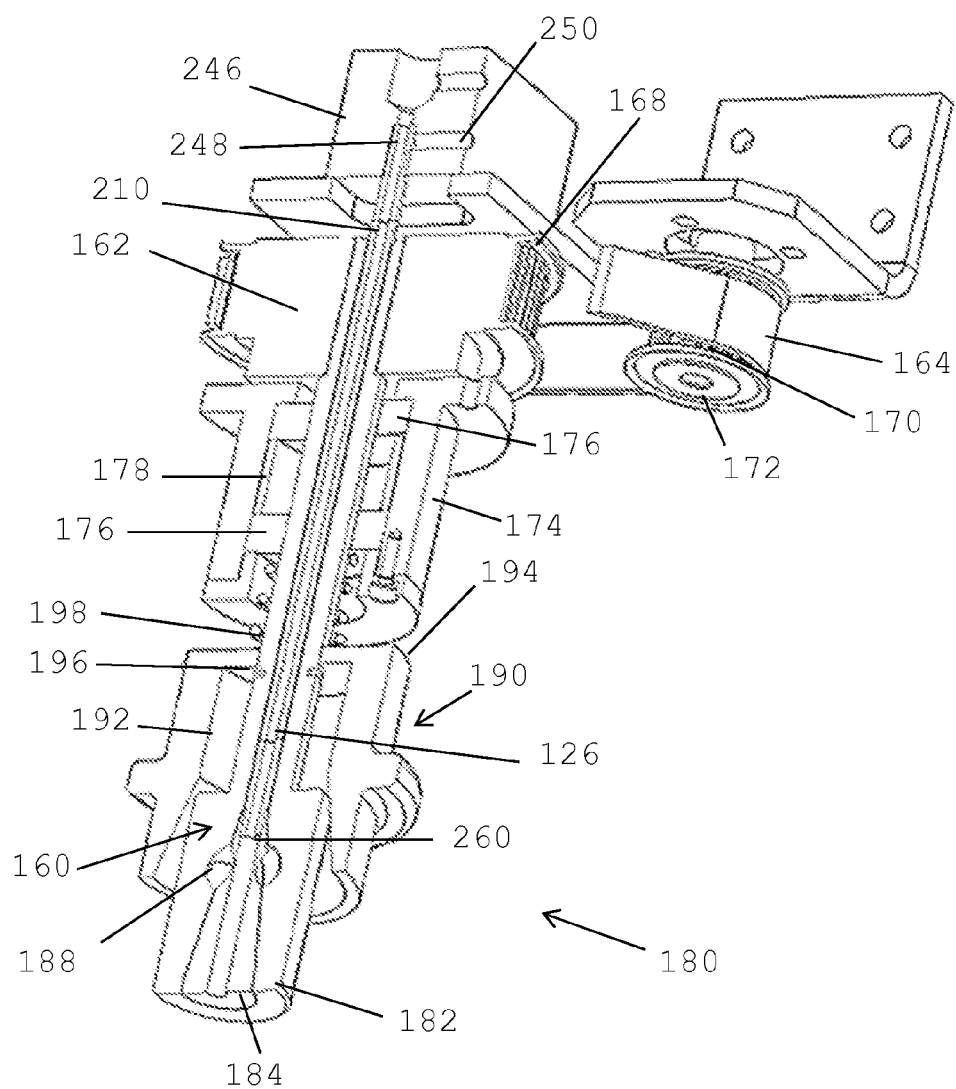
FIG. 15 is a perspective of a portion of the system, including a spindle and a coring bit retaining system, illustrated in cross section taken in a plane including line 12-12 on FIG. 11.

As illustrated in FIG. 12, the cutting action motor 122 is supported by the carriage 130 and movable conjointly with the carriage and the coring bit mount 120. A bearing housing 174 is mounted on the carriage 130 and surrounds a portion of the coring bit mount 120. The bearing housing 174 houses a pair of bearings 176 and a spacer 178 positioned between the bearings so it maintains a minimum spacing between the bearings, as illustrated in FIG. 15. The coring bit mount 120 includes a spindle 160 that extends through the bearing housing 174 and is mounted on the carriage 130 by the bearings 176 for rotation relative to the carriage.

The cutting action motor 122 is adapted to rotate the spindle 160 to produce a rotary cutting action of the single-use coring bit 112. The spindle 160 is connected to the cutting action motor 122 by any suitable transmission system for transmitting output from the cutting action motor to the coring bit mount. In the illustrated embodiment, for example, the spindle 160 includes a pulley 162 connected to the motor 122 by a timing belt 164. The pulley 162 and timing belt 164 include teeth 166 and notches (not shown), respectively, that engage with one another to limit (and preferably substantially eliminate) slippage between the belt and the pulley. Similar teeth 170 are suitably on a pulley 172 on the output shaft of the motor 122 to limit (and preferably substantially eliminate) slippage between the timing belt and the motor pulley. The cutting action motor 122 is suitably a variable speed drive motor that permits the speed at which the single-use coring bit 112 is rotated to be selectively adjusted according to the desired operating parameters for the particular frozen biological sample being aliquotted. For example, the cutting action motor 122 is suitably controlled by the processor which can be configured to operate the cutting action motor in a specified manner (which may vary depending on various factors, including characteristics of the sample and the objectives to be achieved to name a few). Because it limits slippage, the timing belt 164 ensures that motion of the spindle 160, and thus the single use coring bit 112, closely corresponds to the specified manner in which the cutting action motor is operated.

The system 100 includes a coring probe retaining system 180 for retaining the single-use coring probe 110. Various different retaining systems can be used within the scope of the invention. In general, the retaining system allows the single-use probe 110 including a coring bit 112 to be releasably connected to the coring bit mount 120. Those skilled in the art will be familiar with various chucks, collets, threaded connections, and the like that are suitable for releasably retaining a single-use coring bit in the coring bit mount. In the illustrated embodiment, the retaining system 180 is adapted for conversion between a retaining configuration (FIG. 18) and a non-retaining configuration (FIGS. 16-17) by movement of only a single component in substantially only one of the six possible degrees of freedom (i.e., three rotational axes and three translational axes). For example, in the illustrated embodiment the retaining system 180 can be converted between the retaining and non-retaining configuration by moving a only a single components (e.g., a cam 190) linearly, as will be described in more detail below. The ability to quickly and easily convert the retaining system 180 between the retaining and non-retaining configurations using a single, simple movement allows a person operating the system 100 to quickly connect and disconnect single-use coring bits 112 from the coring bit mount 120. It also makes it relatively simple to use a robotic actuator to connect and disconnect single-use coring bits 112 from the system 100.

Referring to FIGS. 12 and 15-18, the end 182 of the spindle 160 of the coring bit mount 120 includes a receptacle 184 and a plurality of retainers 186 (e.g., balls) supported in radially-extending tracks 188. The balls 186 are movable between a retaining position, in which the balls are positioned at an inner end of their respective tracks 188 (see, e.g., FIG. 12), and a non-retaining position, in which the balls are positioned at an outer end of the tracks (see, e.g., FIGS. 10 and 11). The balls 186 are prevented from exiting the tracks 188 at the outer end of the tracks by a cam 190. The balls 186 are prevented from exiting the tracks 188 at the inner end of the tracks by a stop, such as a lip (not shown) at the inner end of the tracks.

The cam 190 in the illustrated embodiment surrounds a portion of the coring bit mount 120. In particular, the cam 190 is configured to surround the end 182 of the spindle 160. For example, the cam 190 suitably has a circumferential sidewall 192 extending down from an upper end 194 of the cam. The cam 190 is suitably mounted on the spindle 160 between the end 182 of the spindle and the bearing housing 174 for sliding movement relative to the spindle between a retaining position and a non-retaining position. For example, in the illustrated embodiment the spindle 160 extends through an opening in the upper end 194 of the cam 190. The cam 190 is slideable vertically on the spindle 160 between a retaining position at the lower end of the cam's sliding path and a non-retaining position at the upper end of the cam's sliding path. The spindle 160 has a stop 196 positioned below the cam 190 to limit downward movement of the cam 190 along the spindle. In the illustrated embodiment, the stop 196 is a washer that is received in a groove on the spindle 160. A biasing member 198 is positioned to bias the cam 190 toward its lower position. In the illustrated embodiment, the biasing member 198 is a helical spring compressed between the upper end 194 of the cam 190 and the bearings 176. The spring 198 biases the cam 190 toward the retaining position and also helps hold the bearings 176 against the spacer 178 in the bearing housing 174.

Figure 16:
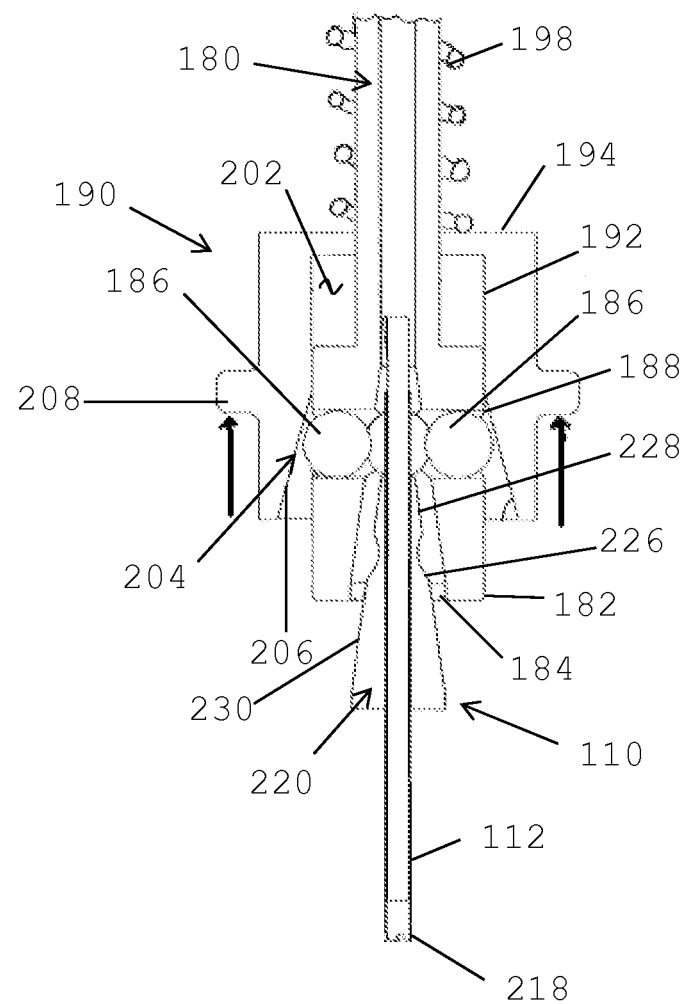
FIGS. 16-18 are side elevations of the coring bit retaining system illustrated in cross-section taken in a plane including line 12-12 on FIG. 11.
Figure 17:
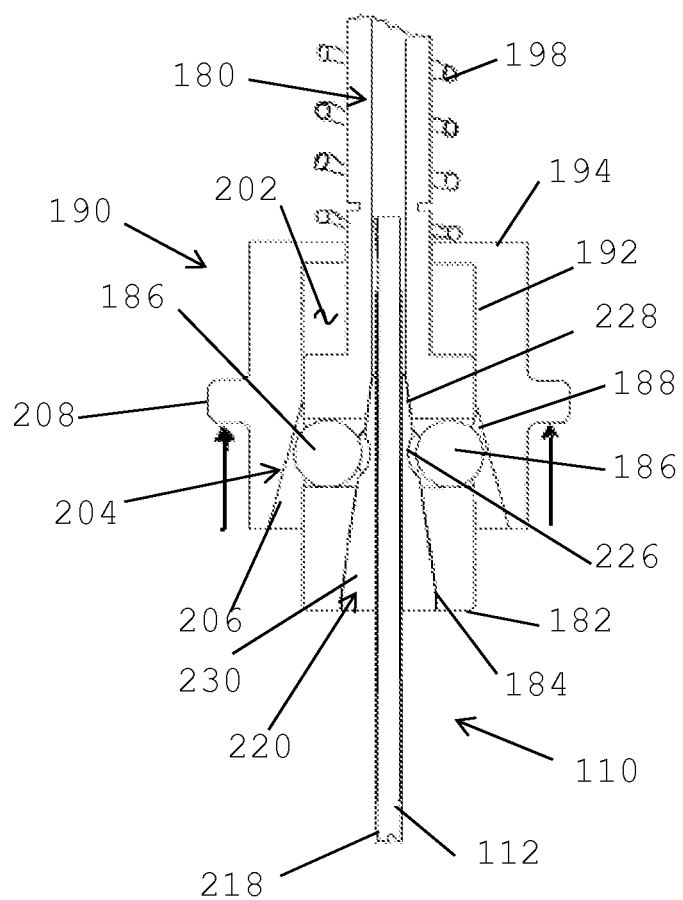
Figure 18:
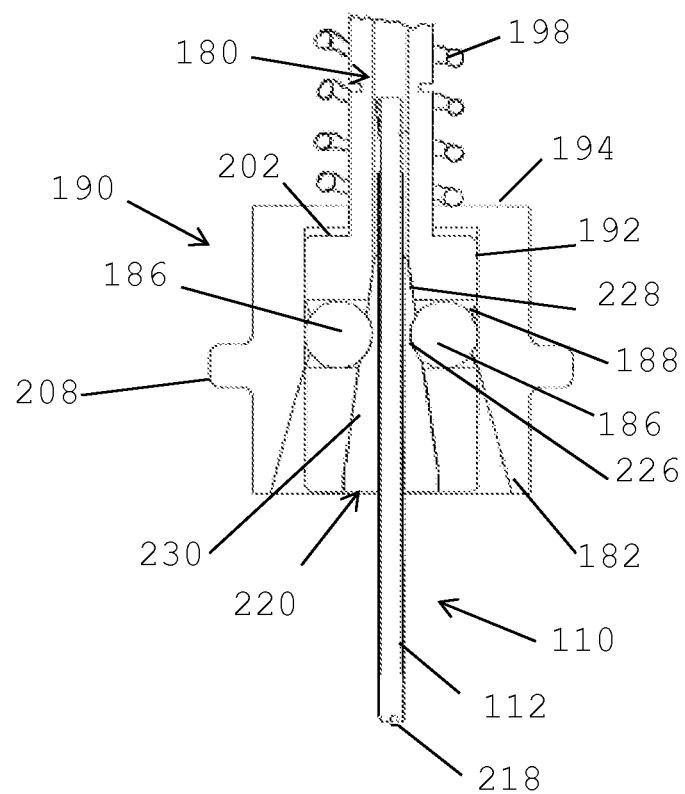

Referring to FIGS. 16-18, the cam 190 includes an annular space 202 for receiving the end 182 of the spindle 160. The annular space 202 and the end 182 of the spindle 160 are suitably configured for close-fitting reception of the end in the annular space. The annular space 202 and the end 182 can be generally cylindrical, as illustrated for example. The cam 190 includes a camming surface 204. In the illustrated embodiment the camming surface 204 includes a tapered surface 206. The tapered surface 206 is suitably positioned at the distal end of the cam 190. The tapered surface 206 extends from a narrower end adjacent the annular space 202 at the upper end of the cam 190 to a wider end at the lower end of the cam. The tapered portion of the camming surface 206 is positioned to contact the balls 186 and define the maximum extent to which the balls can be positioned radially outward in their tracks 188.

When the cam 190 is in its retaining position (FIG. 18), the cam 190 holds the balls 186 in retaining positions at the inner ends of their tracks 188. When the balls 186 are in their retaining positions, there is a relatively smaller amount of space between the balls for retaining the coring bit 112 in the spindle 160. The cam 190 can be moved upward against the bias of the spring 198 by a user toward the non-retaining position. As the cam 109 is moved toward its non-retaining position (FIGS. 16 and 17), the tapered portion of the camming surface allows the balls 186 to move farther toward their non-retaining position at the radially outward ends of their tracks 188. For example, a force exerted by a user pulling the coring bit 112 out of the mount 120 can move the balls 186 outwardly in the tracks 188. When the balls 186 are in their non-retaining positions, there is a relatively larger space between the balls for releasing the single-use coring bit 112 from the spindle 160. When the cam 190 has been moved upwardly sufficiently to allow enough separation between the balls 186 to release the single-use coring bit 112, the cam has reached its non-retaining position.

The cam 190 suitably includes a grip 208 to facilitate manual movement of the cam toward its non-retaining position by a person operating the system 100. In the illustrated embodiment, for example, the grip 208 includes a flange extending radially outward from the outer surface of the cam sidewall 192 at a position above the lower end of the cam 190. Thus, a user can hold the cam sidewall 192 below the flange 208 and push up against the flange 208 to move the cam 190 upward toward the bearing housing 174 against the bias of the spring 198 to release the single-use coring bit 112 from the spindle 160. In a fully automated system, the system can move the grip relative to another structure (e.g., the edge of an opening for receiving used coring probes) or include an additional actuator (not shown) to move the cam 190 between its retaining and non-retaining positions.

The receptacle 184 in the end 182 of the spindle 160 is tapered from a narrower proximal end to a wider distal end. The single-use coring probe 110 is received in the receptacle 184 in the end 182 of the coring bit mount 120. The single-use coring probe 110 includes a hollow coring bit 112 (e.g., hollow tube having a cutting tip) for taking a frozen sample core from the frozen sample and an ejector 210 adapted to eject the frozen sample core contained in the coring bit 112 from the end of the coring bit. The ejector 210 is movable from a retracted position to an extended position and operable to push any frozen sample core retained in the coring probe 112 out of the coring probe as it moves from the retracted position to the extended position. For example, the distal end of the ejector 210 suitably moves from a position within the hollow coring bit 112 and spaced from a distal end of the coring bit to a position beyond the distal end of the coring bit as the ejector moves to the extended position.

Figure 19:
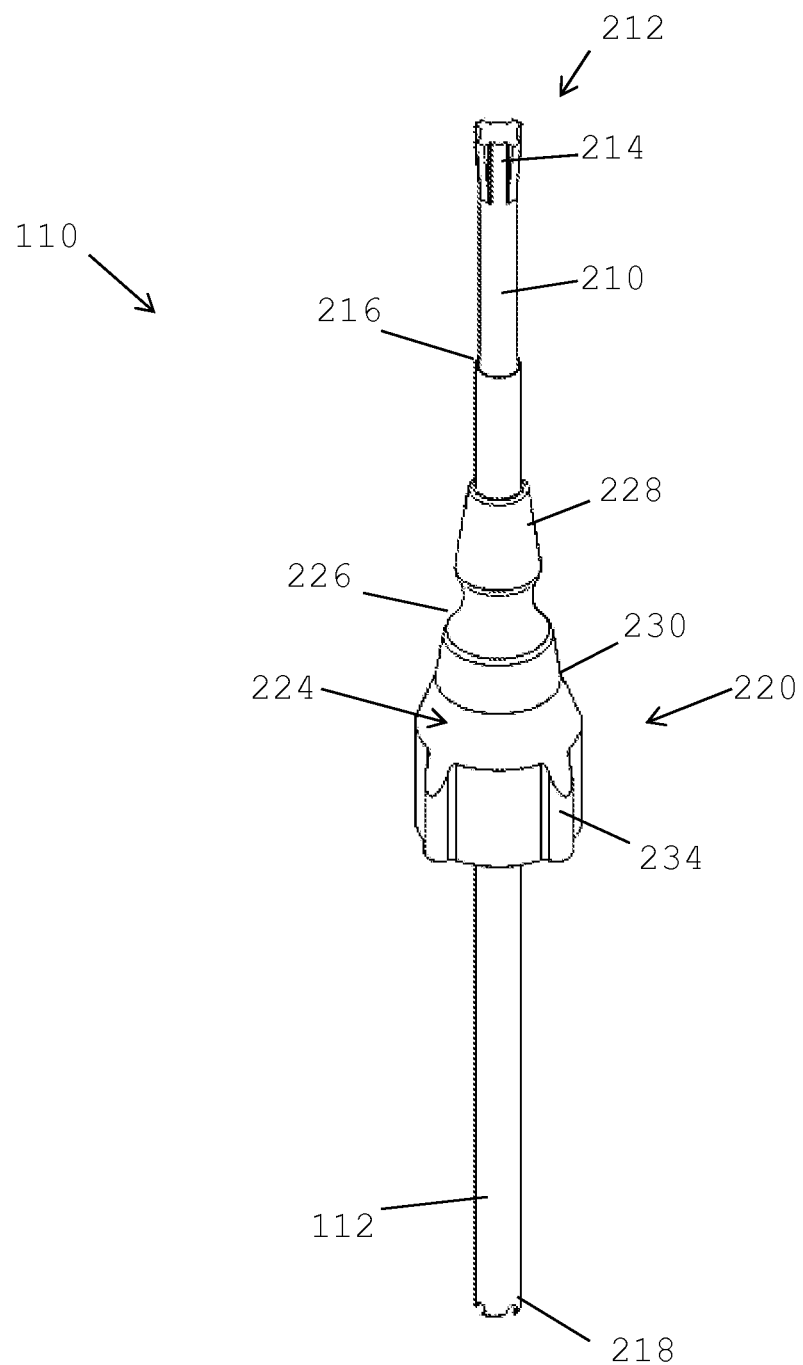
FIG. 19 is a perspective of another embodiment of a single-use coring probe.
Figure 20:
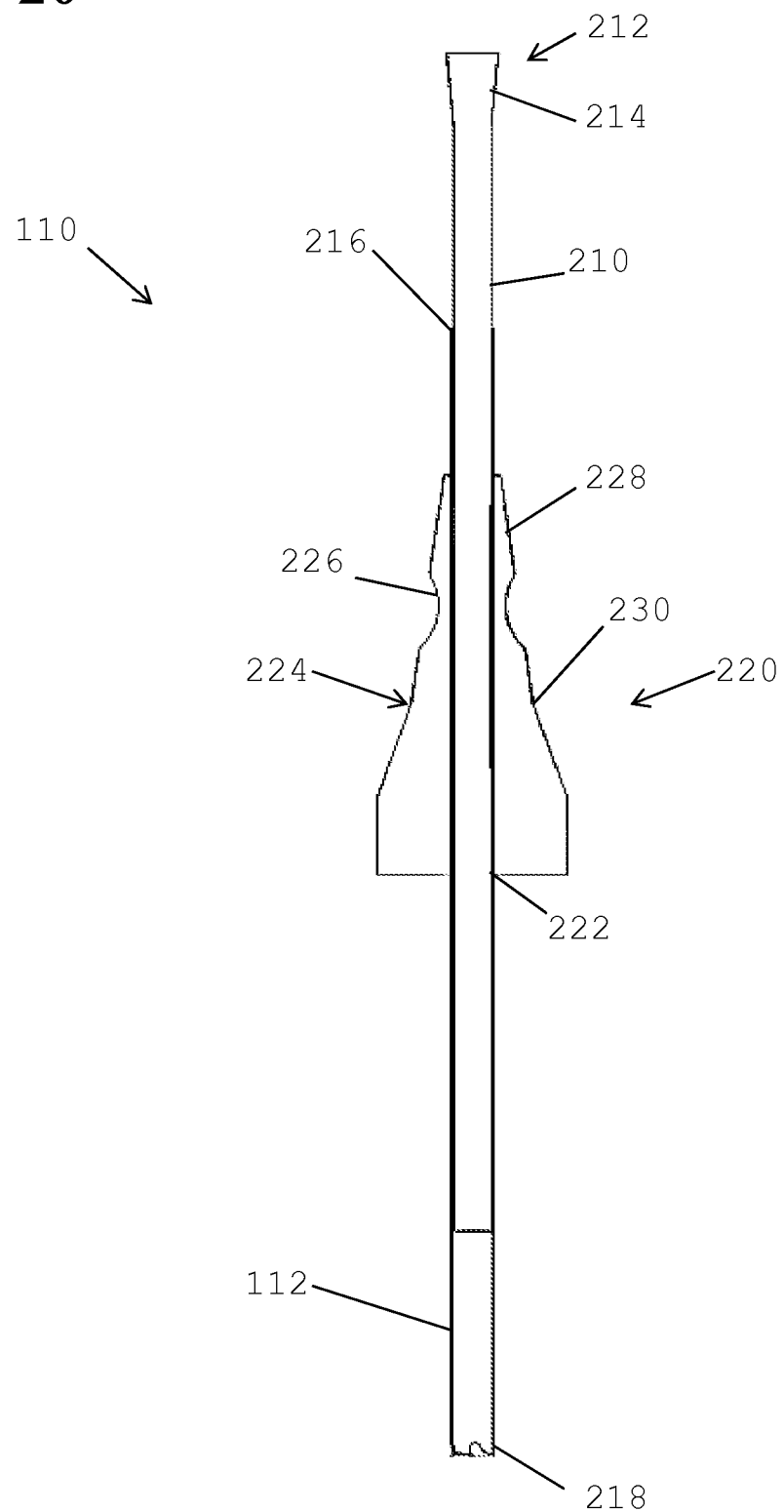
FIG. 20 is a side elevation of the single-use coring probe shown in FIG. 19 illustrated in cross-section.
Figure 21:
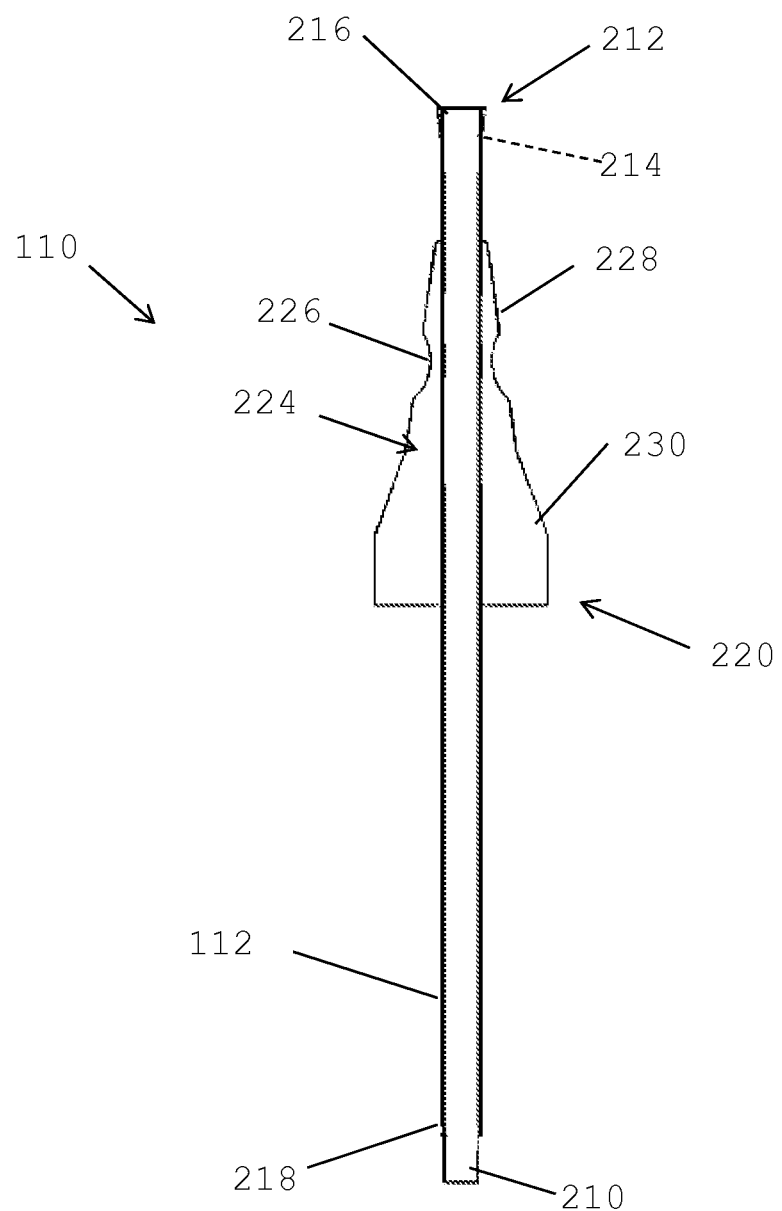
FIG. 21 is a side elevation of the single-use coring probe after it has been used.
Figure 22:
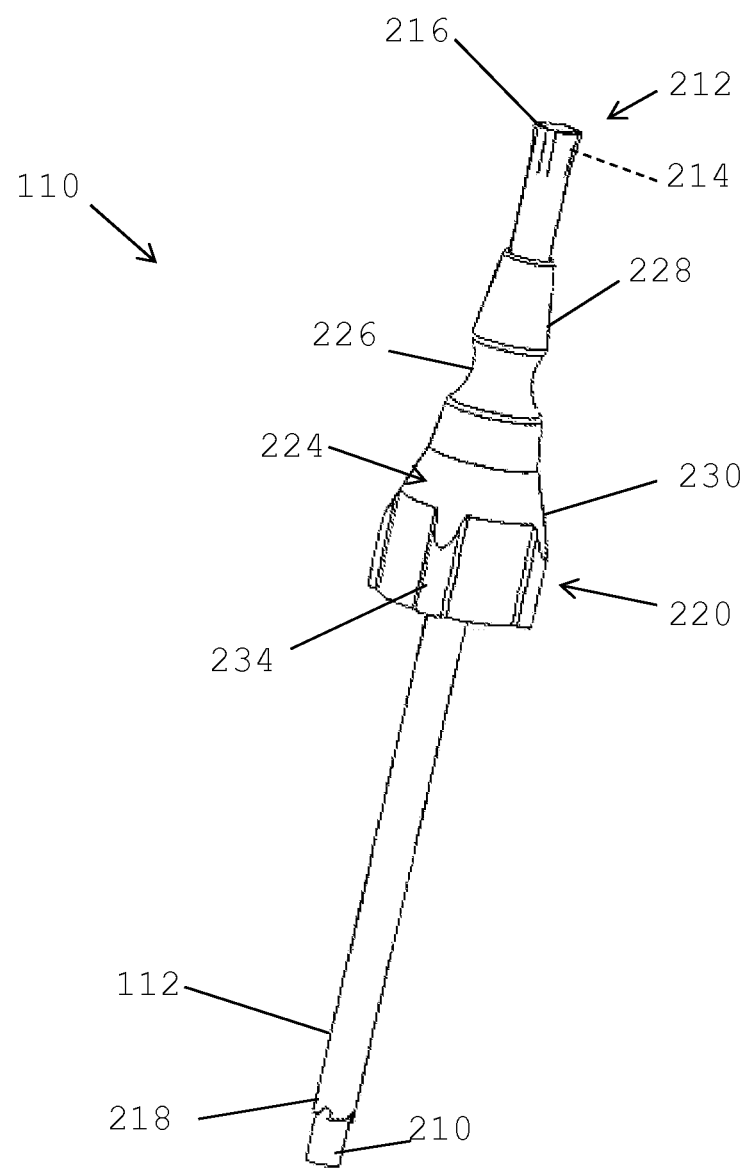
FIG. 22 is a perspective of the single-use coring probe after it has been used.

Except as noted, the single-use coring probe 110 is suitably substantially identical to the single-use coring probe 12 described above. Referring to FIGS. 19-22, the single-use coring probe 110 suitably includes a locking mechanism 212 adapted to discourage re-use of the coring probe to ensure that the coring probe is used only once, thereby preventing the possibility for carryover or contamination between samples. As seen in FIG. 19, the locking mechanism 212 comprises a plurality of wedge-shaped ribs/barbs 214 extending radially from the exterior surface of the ejector 210. In the illustrated embodiment, the locking mechanism 212 includes a plurality of wedge-shaped ribs 214 (e.g., four ribs). The ribs 214 are adapted for engagement with the hollow coring bit 112 during movement of the ejector from the retracted position to the extended position. The ribs 214 are positioned on a portion of the ejector that extends above the proximal end 216 of the coring bit 112 when the ejector is in the retracted position. The ribs 214 in the illustrated embodiment are not in contact with the coring bit 112 when the ejector 210 is in the retracted position.

When the ejector 210 is moved from the retracted position (FIGS. 19 and 20) to the extended position (FIGS. 21-22) to eject the frozen aliquot, the ribs 214 are inserted into the proximal end of the coring bit 112. The ribs 214 are configured to stick in the proximal end 216 of the coring bit 112 and resist movement of the ejector 210 back from the extended position back toward the retracted position. For example, the ribs 214 are suitably sized and shaped so the ribs must be jammed into the proximal end of the coring bit (e.g., deforming at least one of the ribs and the proximal end 216 of the coring bit) so that the portion of the ejector 210 having the ribs cannot easily be extracted from the coring bit. Thus, use of the ejector 210 to eject a frozen sample core from the coring bit 112 results in automatic locking of the ejector 210 in the extended position, which prevents or at least provides a substantial deterrent against use of the same coring probe 110 to obtain a frozen sample core from any additional frozen samples.

Referring to FIGS. 16-22, the single-use coring probe 110 includes a coupling 220 adapted to connect the probe and the coring bit 112 thereof to the coring bit mount 120. In the illustrated embodiment, the coupling 220 is secured to the outer surface of the coring bit 112 between its proximal and distal ends 216, 218. For example, the coupling 220 suitably has a central opening 222 (e.g., bore) that receives the coring bit 112 (e.g., via an interference fit that securely holds the coring bit in the coupling). In the illustrated embodiment, the hollow coring bit 112 extends completely through the coupling 220 from one end of the coupling to its opposite end. The coupling 220 can be adhered to the coring bit 112 (e.g., using glue or other adhesives), overmolded onto the coring bit, and/or may include one or more projections extending into an opening in the side of the coring bit to secure the coupling to the coring bit. The coupling 220 is sized and shaped to be received in the receptacle 184 at the end 182 of the spindle 160 of the coring bit mount 120. The coupling 220 and the receptacle 184 are each suitably symmetrical about their central axes to facilitate connecting the coupling to the coring bit mount 120 without any concern about the rotational orientation of the coring probe 110 on its axis relative to the orientation of the coring bit mount 120.

The coupling 220 has a body 224. In the illustrated embodiment, the body includes a tapered portion. For example, the entire body 224 is suitably generally tapered. The tapered body 224 has a narrower proximal end and a wider distal end. The tapered body 224 is sized and shaped for close-fitting reception in the receptacle 184 at the end of the spindle 160. A circumferential groove 226 extends radially into the body 226 around an outer surface of the body 224 and separates the body into an upper portion 228 and a lower portion 230. The groove 226 is configured to receive the balls 186 to retain the coring probe 110 in the coring bit mount 120. When the balls 186 are in the non-retaining position, the upper portion 228 of the coupling 220 can be inserted past the balls 186 into the coring bit mount 120 until the groove 226 is aligned with the balls. The tapered shape of the coupling 220 facilitates inserting the upper portion 228 of the coupling between the balls 186 by gradually moving the balls radially outward in their tracks 188 if needed. When the balls 186 are in their retaining positions they are received in the groove 226 on the coupling 220 and thereby retain the coupling in the coring bit mount 120 by resisting movement of the coring probe 110 either downward or upward relative to the spindle 160.

The coupling 220 can include one or more keys or other suitable features engageable with the coring bit mount 120 to hold the coring bit 112 in substantially fixed orientation relative to the spindle 160 to facilitate transmission of rotational movement of the spindle to the coring bit. In the illustrated embodiment, for example, the coupling includes a plurality of splines 234 (e.g., four splines). The splines 234 are suitably configured to engage stops (not shown) extending radially inward from the coring bit mount 120 so any initial rotation of the single-use coring bit 112 relative to the coring bit mount causes the stops to engage the splines and limit further slippage between the single-use coring probe 110 and the coring bit mount. Thus, the splines 234 or other keying structure suitably operates in conjunction with the timing belt 164 to ensure the movement of the single-use coring bit 112 closely corresponds to the movement of the cutting action motor 122. Another option to limit slippage between a single-use coring probe and the coring bit mount is to include one or more flat faces (not shown) on the coupling and provide corresponding structures on the coring bit mount to use the flat faces to apply torque to the coring probe. For example, the coupling can have a polygonal (e.g., hex-shaped) cross sectional shape including a plurality of flat faces (e.g., six) extending around the circumference of the coupling and the coring bit mount can have fingers adapted to engage some or all of the flat faces.

The coupling 220 is adapted to limit transfer of heat between the coring bit 112 and the system 100. For example, the coupling 220 is suitably made from a material having a relatively low thermal conductivity. The single-use coring bit 112 is suitably pre-cooled before the coring operation. This pre-cooling can be accomplished in various ways, such as by keeping the coring probe 110 in a cold location until it is ready for use, exposing the coring bit 112 to a coolant (e.g., liquid nitrogen, the vapor above liquid nitrogen, dry ice, a slurry containing dry ice and alcohol or another liquid, cold gas, etc.) just before use, either by immersing the coring bit in the coolant or by exposing the coring bit to a stream including the coolant. Pre-cooling can include actively cooling an individual coring bit 112 to reduce its temperature just before use or it can include keeping a set of coring probes 110 in an environment that ensures all the coring bits 112 in the set are already at a desirably low temperature when an individual coring probe from the set is selected for use in a coring process. The pre-cooling system can be adapted to ensure the temperature of the coring bit 112 is no more than about −20 C when the coring bit first contacts the frozen sample, such as no more than about −40 C when the coring bit first contacts the frozen sample, such as more than about −60 C when the coring bit first contacts the sample, such as no more than about −80 C when the coring bit first contacts the sample.

The low thermal conductivity of the coupling limits heating of the coring probe 112 by the coring bit mount 120 and the rest of the system 100, which has a substantially larger thermal mass and which would be much more difficult to maintain at such a low temperature because of the energy requirements to keep such a large thermal mass at such a low temperature and because of difficulties operating motors and other components of the system at such a low temperature. The thermal conductivity of the coupling 220 is suitably no more than about 50 w/mK, more suitably no more than about 10 w/mK, more suitably in the range of about 0.001 w/mK to about 5 w/mK, still more suitably no more than about 0.001 w/mK to about 2 w/mK. Suitable materials having a low thermal conductivity that can be used for the coupling 120 include plastics, ceramics, rigid foams (e.g., cast urethane), Stainless Steel, graphite, carbon fiber, metal matrix composites (e.g., steel graphite combinations) honeycomb skinned materials, etc. The coupling can include an air or vacuum-filled void space to provide additional resistance to heat transfer through the coupling. For example, the coupling 220 can be made of a foam or other porous material including many small voids. Another option is to construct the coupling so it includes multiple walls (not shown) spaced from one another. The inclusion of one or more void spaces in the coupling can allow the effective thermal conductivity to be reduced to the levels set forth above even when the coupling is made from a base material having a higher thermal conductivity. The coupling can also be made from a non-insulating material having a higher thermal conductivity within the scope of the invention.

Figure 13:
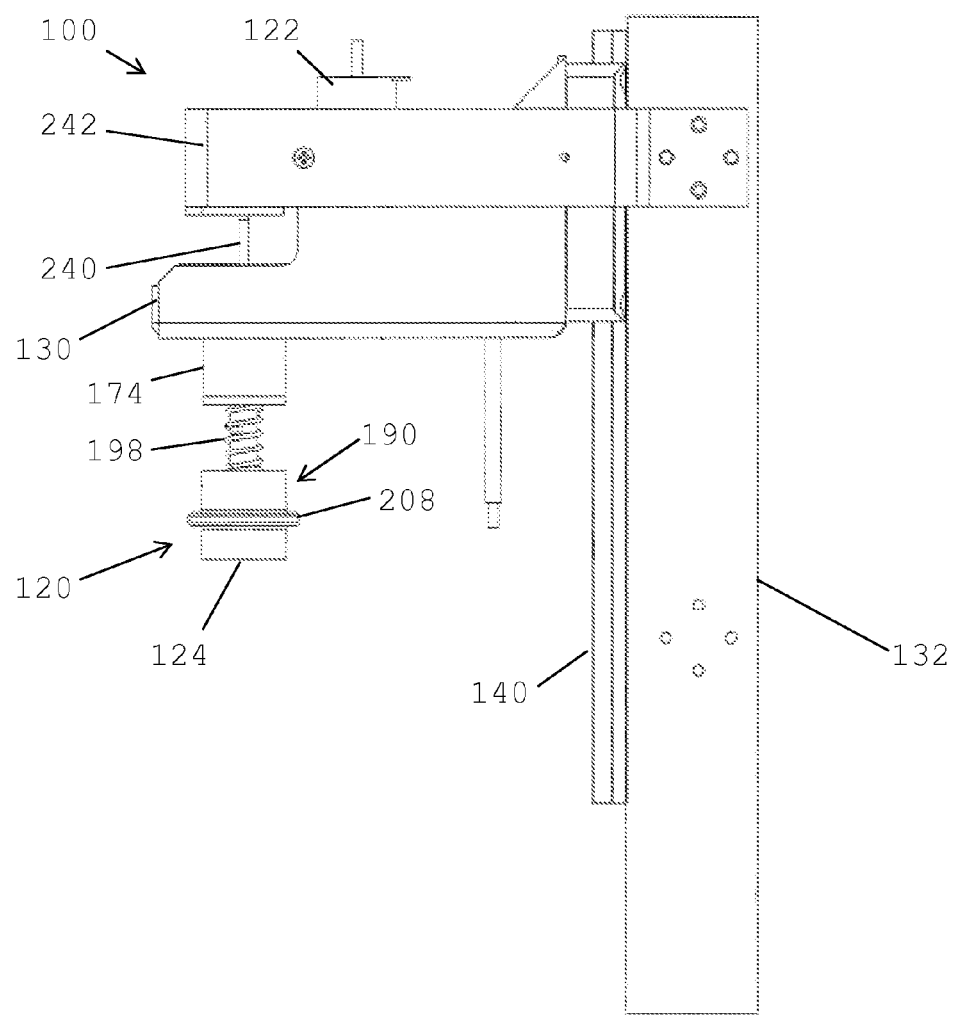
FIG. 13 is a side elevation of the system.
Figure 14:
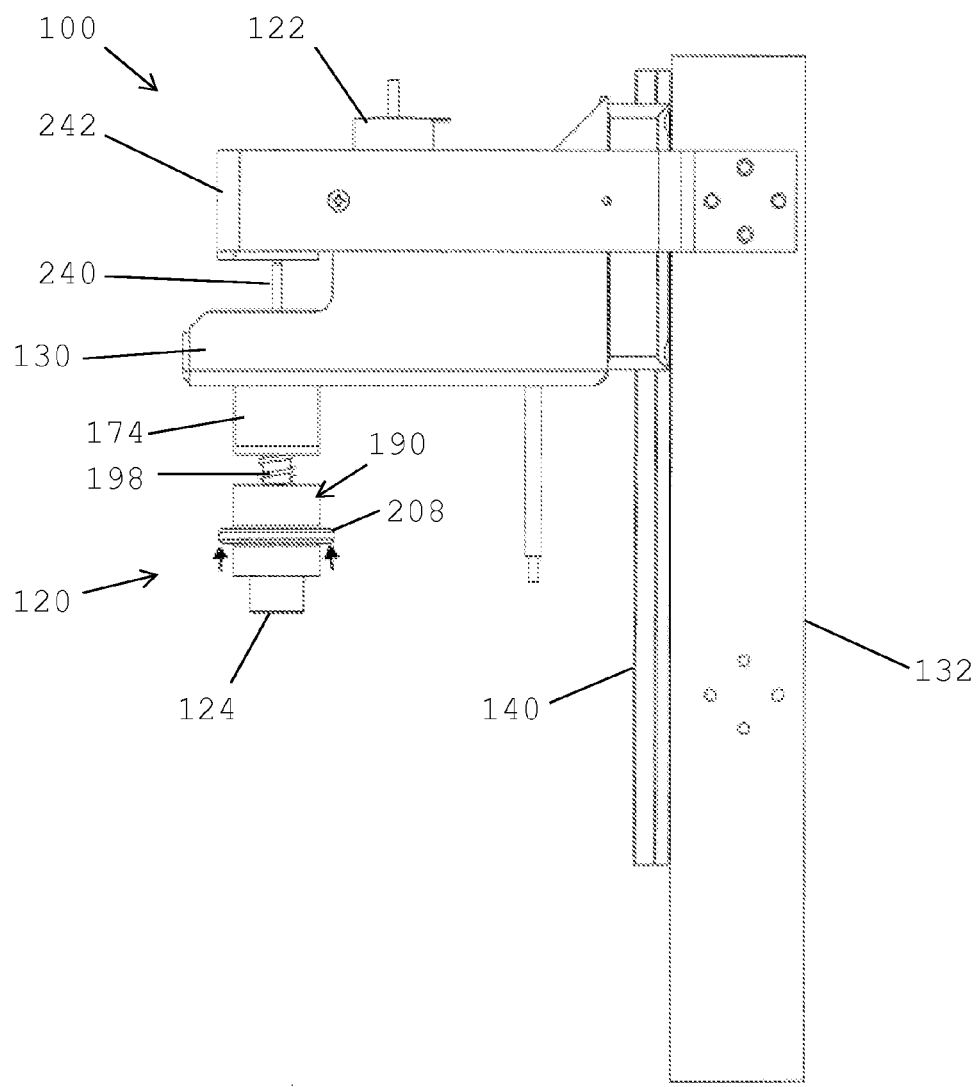
FIG. 14 is a side elevation similar to FIG. 13 showing a coring bit retaining system after it has been moved to a non-retaining configuration.

The system 100 includes an ejection system to eject the frozen sample core from the single-use coring bit 112. In the illustrated embodiment, for instance, the ejection system includes a plunger 240 for actuating the ejector 210 to eject a frozen sample core from the coring bit 112. As illustrated in FIGS. 13-15, the plunger 240 is a rod attached at one end to a bracket 242 that is fixed relative to the support 132 so that movement of the carriage 130 that supports and moves the coring bit mount 120 and any coring probe 110 held therein produces movement of the plunger relative to the components of the coring bit mount 120, including the spindle 160 and the coring bit 112. The opposite end of the plunger 240 extends into an opening 126 in the coring bit mount 120. In the illustrated embodiment, the bracket 242 supports a platform 244. A mounting block 246 is supported by the platform 244. The mounting block 246 includes a receptacle 248 configured to receive a proximal end of the plunger 240. The plunger 240 is fixed in the mounting block 246 by any suitable connector, such as by a set screw (not shown) extending through a bore 250, or any other suitable connection. The plunger 240 is positioned so its distal end 260 is spaced from the ejector 210 of a coring probe 110 held by the coring bit mount 120 when the carriage 130 is in a lowered position (e.g., a position in which the coring bit 112 is inserted into the sample) and so the distal end of the plunger will contact the ejector 210 and move it from its retracted position to its extended position as the carriage is raised from the lowered position to it fully raised position.

Once the system 100 ejects a frozen sample core from the single-use coring probe 110, the single-use coring probe is disabled (e.g., by the ribs on the end of the ejector being jammed into the end of the coring bit 112 to lock the ejector in its extended position).

Figure 23:
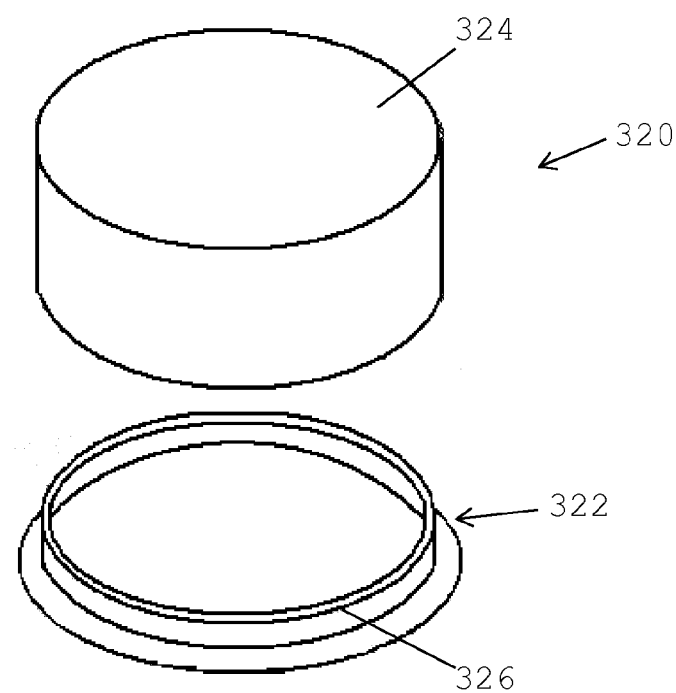
FIG. 23 is an exploded perspective of a tissue sample container.

FIGS. 23-29 illustrate some embodiments of a tissue sample container and mount that can be used with the handheld coring device 10 or other suitable coring device, such as an automatic or robotic coring device. Referring to FIG. 23, the tissue sample container, generally designated 320, includes a shallow base 322 and a relatively taller cap or lid 324. The lid 324 can be securely fastened to the base 322 by any suitable means, such as by interengaging threads or other means known in the art. As illustrated, the tissue sample container 320 is generally cylindrical and has a circular cross sectional shape. However, the container 320 can be any shape, such as hexagonal, rectangular, or any other desirable shape (e.g., to better fit the size and shape of the tissue sample being stored). The base 322 is suitably configured for attachment to a slide sectioning device (not shown), such as a cryotome or a microtome, or other commonly available tissue sectioning device. Suitable sectioning devices are well known to those skilled in the art of research involving study of tissue samples and do not need to be described further herein. In the embodiments described below, the base 322 includes alternative constructions permitting the base to be attached to a slide sectioning device. The base 322 of the container 320 is sometimes referred to as a tissue carriage herein, because it can be used to transport frozen tissue from a storage location in frozen storage to a sectioning device.

Figure 24A:
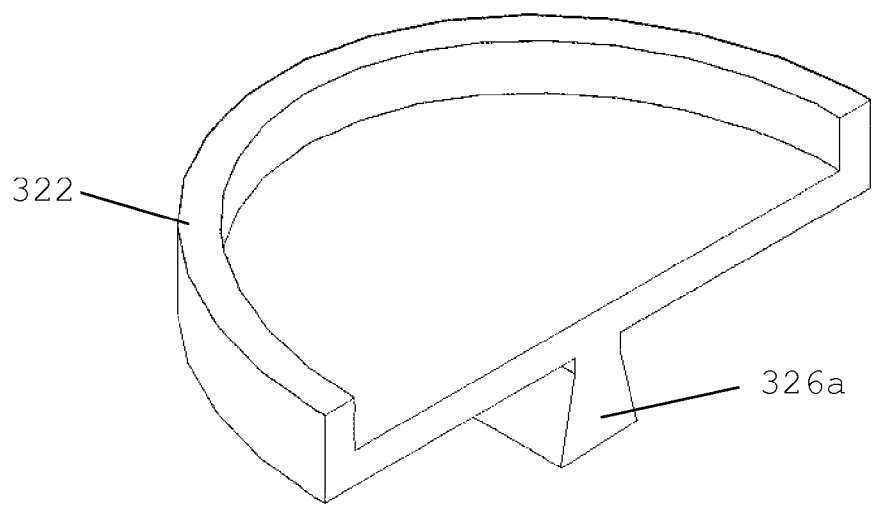
FIG. 24A is cross section showing a first embodiment of a base of the tissue sample container.
Figure 24B:
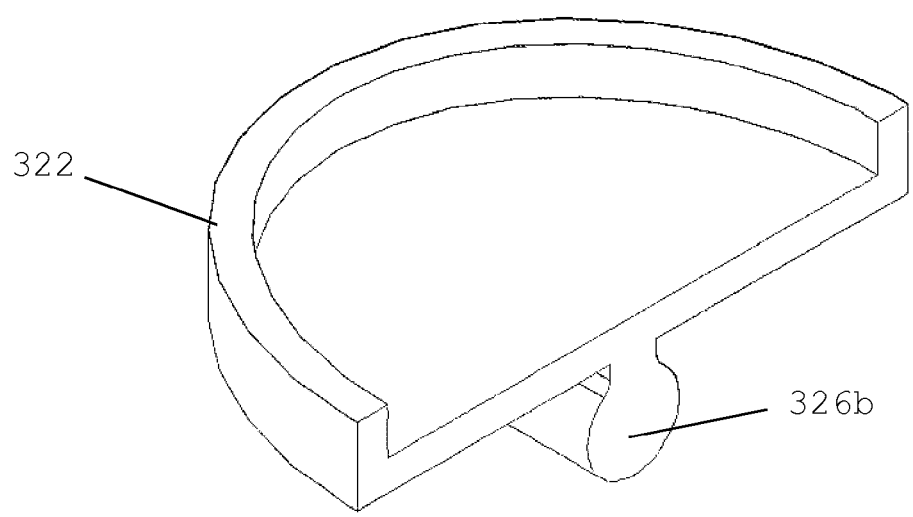
FIG. 24B is a cross section showing a second embodiment of a base of the tissue sample container.
Figure 25A:
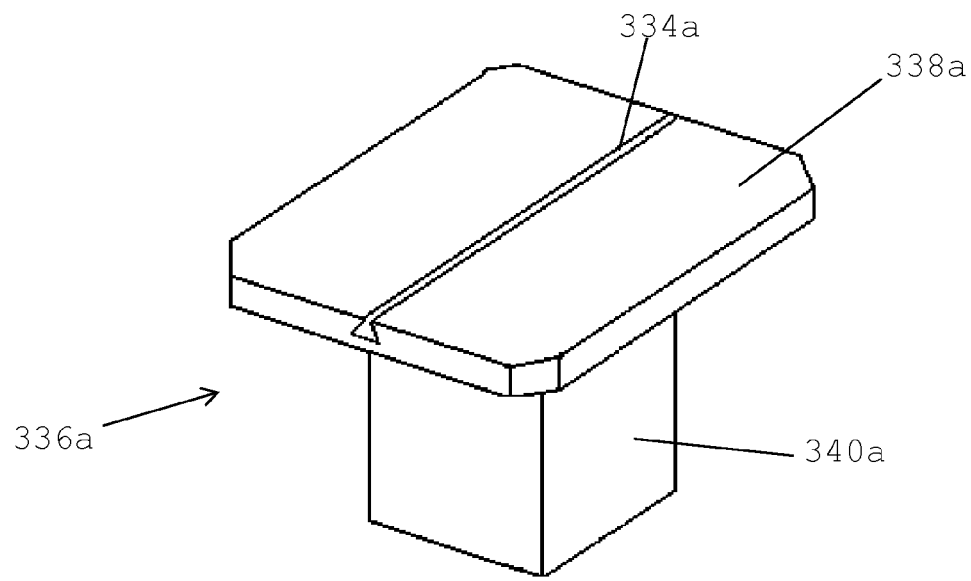
FIG. 25A is a perspective of a first embodiment of a container mount.
Figure 25B:
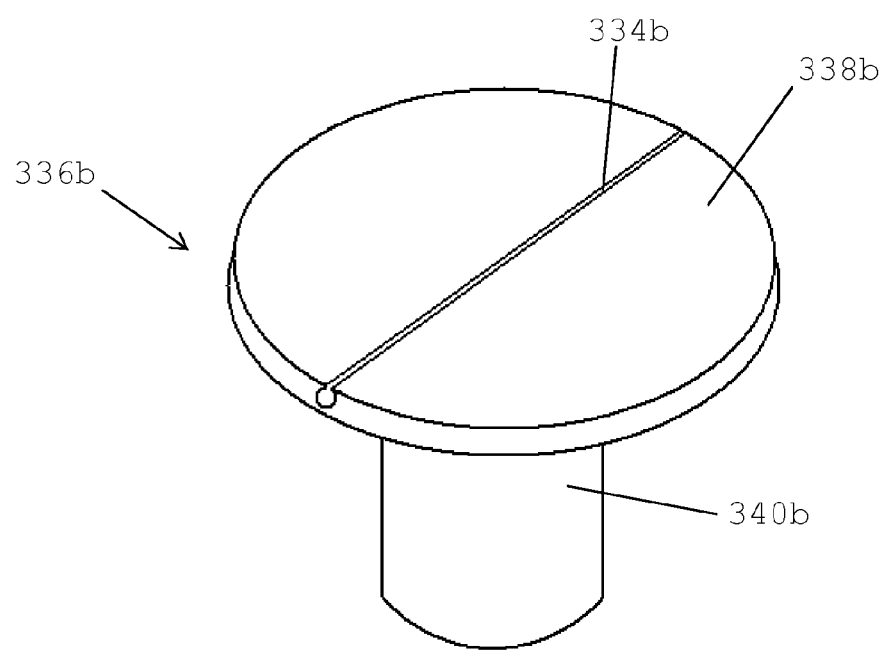
FIG. 25B is a perspective of a second embodiment of a container mount.

In the embodiments illustrated in FIGS. 24A and 24B, the base 322 or tissue carraige includes a rail 326a, 326b configured to engage with a corresponding groove 334a, 334b on a mount 336a, 336b (see corresponding FIGS. 25A and 25B) that can be secured to the slide sectioning device. Each exemplary mount 336a, 336b shown in the drawings includes a generally planar upper portion 338a, 338b and a post 340a, 340b extending from the planar upper portion. The post 340 is sized and shaped for securing the post to a slide sectioning device, such as by being received in a standard vise or clamp of the device. As seen in FIG. 24A and corresponding FIG. 25A, the rail 326a and the groove 334a both comprise a dovetail shape. Thus, the dovetail groove 334a receives the dovetail rail 326a, thereby securing the base 322 to the mount 336a and thus the slide sectioning device. Similarly, as seen in FIG. 24B and corresponding FIG. 25B, the rail 326b and the groove 334b both comprise a "lollipop" shape. Thus, the lollipop groove 334b receives the lollipop rail 326b, thereby securing the base 322 to the mount 336b and thus the slide sectioning device. As illustrated, the upper portion 338a and the post 340a of the mount 336a are generally rectangular, and the upper portion 338b and the post 340b of the mount 336b are generally circular. However, the upper portion 338 and post 340 of the mount 336 can have any shape, and the upper portion and post need not be the same shape. Likewise, the rail and groove can have different cross sectional shapes within the scope of the invention. Also, the rail could be replaced by one or more tabs sized and shaped to be received in the groove to connect the base to the mount.

Figure 26A:
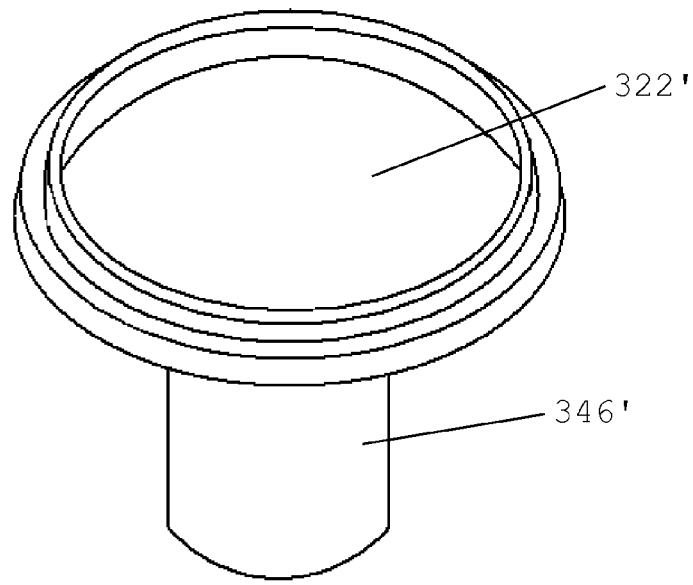
FIG. 26A is a perspective of a first embodiment of a tissue sample container having an integral mount.
Figure 26B:
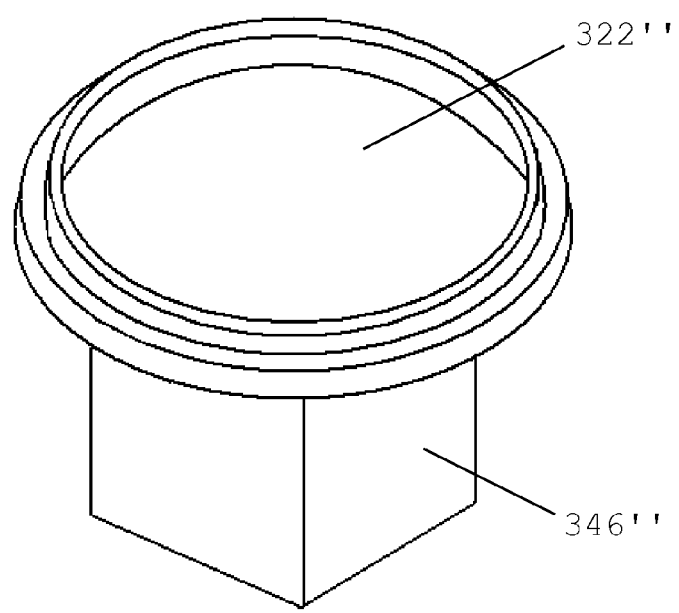
FIG. 26B is a perspective of a second embodiment of a tissue sample container having an integral mount.

FIGS. 26A and 26B illustrate bases 322', 322" for the container 320 having a mount or post 346', 346" integrally formed therewith. The posts 346', 346" can be secured to a slide sectioning device, such as by being received in a vise or clamp of a microtome. In FIG. 26A, the post 346' is generally circular, and in FIG. 26B, the post 346" is generally rectangular. However, the post can have any shape within the scope of the present invention.

Figure 27:
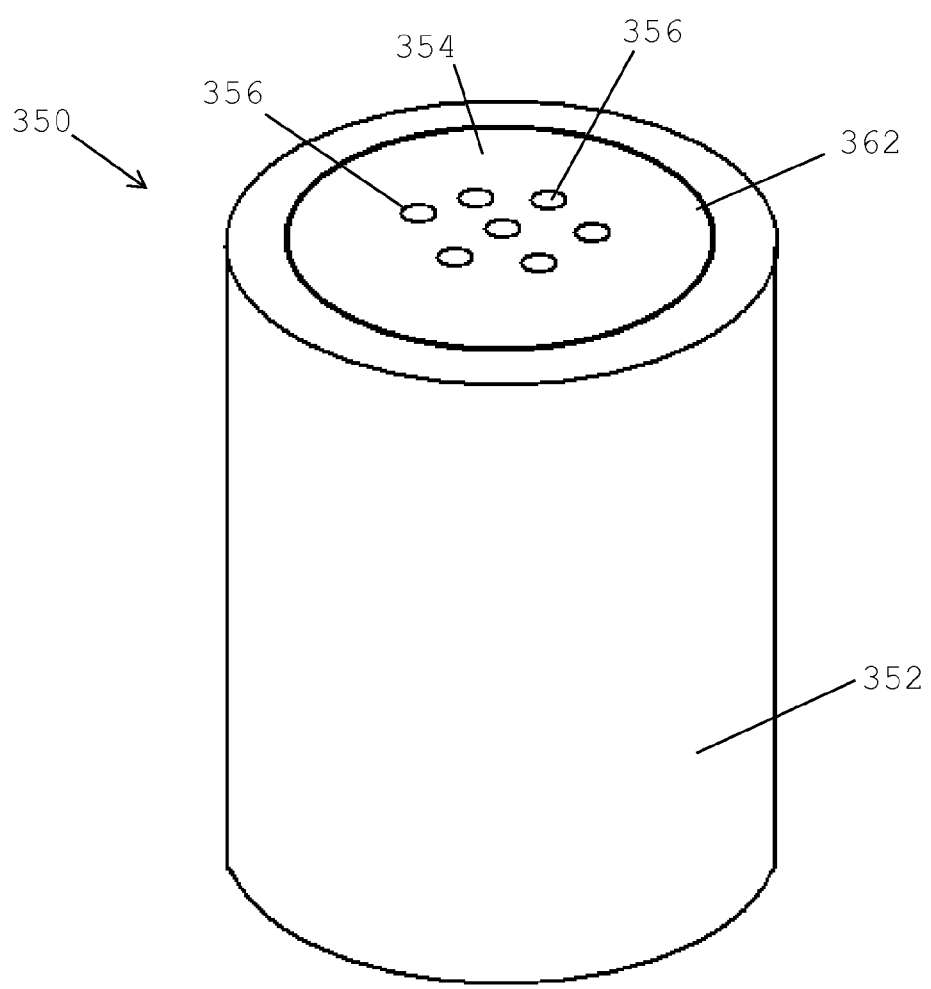
FIG. 27 is a perspective of one embodiment of a vacuum mount for a tissue sample container.
Figure 28:
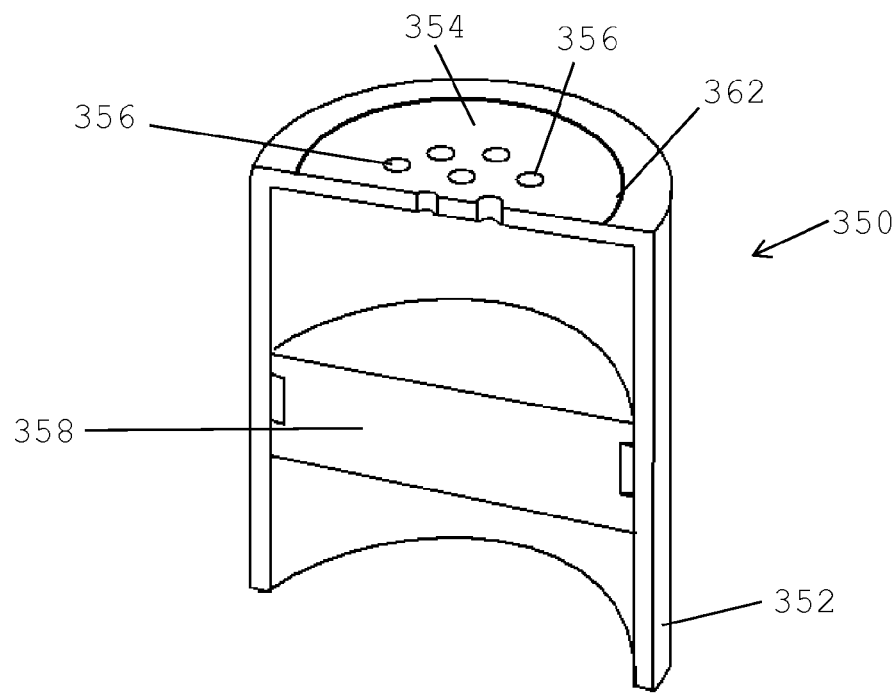
FIG. 28 is a cross section of the vacuum mount.
Figure 29:
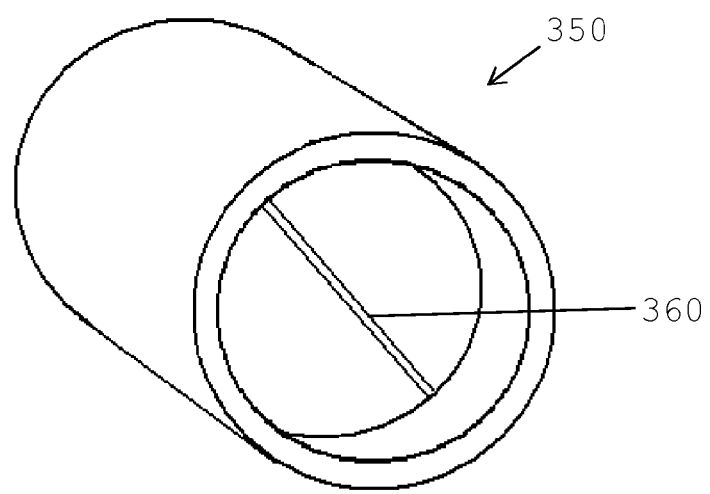
FIG. 29 is a perspective of a piston of the vacuum mount.

FIGS. 27-29 illustrate a vacuum chuck 350, which can be used to secure the container 320, and in particular the base 322 or tissue carriage thereof, to a slide sectioning device. The vacuum chuck 350 includes a hollow post 352 that can be secured to a slide sectioning device, such as by being received in a vise or clamp of a microtome. An upper surface 354 of the vacuum chuck 350 includes multiple ports 356. A piston 358 is received in the hollow post 352 and is moved away from the upper surface 354 by turning a positioner 360 with a tool, such as a screw driver, to move the piston away from the ports 356. This creates a lower pressure in the hollow post, thereby allowing the base of a container 320 to be secured to the upper surface 354 of the vacuum chuck 350 by placing the bottom of the container adjacent the ports and moving the piston to form a suction seal between the vacuum chuck and the base of the container. The vacuum seal can be ensured by use of an O-ring 362. The vacuum is released by moving the piston 358 back towards the upper surface 354. Other configurations for moving the piston are within the scope of the present invention, such as movement by a threaded rod attached to the piston.

Tissue is stored in the tissue sample container 220 on top of a layer of OCT, paraffin, saline, gelatin, buffer, agar, cell culture media, water, or other suitable sacrificial material such as other bio-inert materials suitable to support and attach tissue to the container. In order to prepare the tissue sample container 320 to receive a tissue sample, first a layer of the sacrificial material is placed in the container. In one embodiment, the tissue container 320 can be prefilled with a sacrificial layer for easy use, with a selectively removable sealing structure such as a removable plastic liner covering the base 322 to retain the prefilled sacrificial layer in the container. Before the tissue sample can be placed on the sacrificial layer, the sacrificial layer must be able to support the tissue above a bottom of the container 320. Some materials that can be used for the sacrificial layer are suitably able to support the tissue at room temperature and/or right away. Other materials must set and/or solidify (e.g., freeze) before they are able to support the tissue. If needed, the container can be placed in cold storage until the sacrificial layer is frozen before the tissue is placed on it. Once the sacrificial layer is in a state such that it can support tissue above the bottom of the container, the tissue sample can be placed on the sacrificial layer. The tissue sample can be either frozen or fresh tissue. In the case of frozen tissue, a small amount (e.g., 5 mL) of a secondary medium can be applied to the top of the sacrificial layer to foster adherence of the tissue sample to the sacrificial layer and thus to the container. This may be desirable when the sacrificial layer is also frozen. Suitably, the secondary medium can comprise the sacrificial material at room temperature or in a liquid state. The tissue sample is then placed on the wetted surface, which will secure the tissue sample to the sacrificial layer and thus to the container 320. If the tissue sample is fresh, the rewetting can be omitted without affecting adherence because of the moisture available in the fresh tissue. The tissue sample is suitably above the level of the base 322 of the container 320 when placed on the sacrificial material to facilitate cutting slides from the top of the tissue without removing the tissue from the container. The container 320 is then placed in cold or frozen storage to freeze the tissue sample until a sample of the tissue sample is required. As used herein, cold storage or frozen storage refers to a storage system maintained in the range of about 0 to about −192 degrees centigrade.

Figure 30:
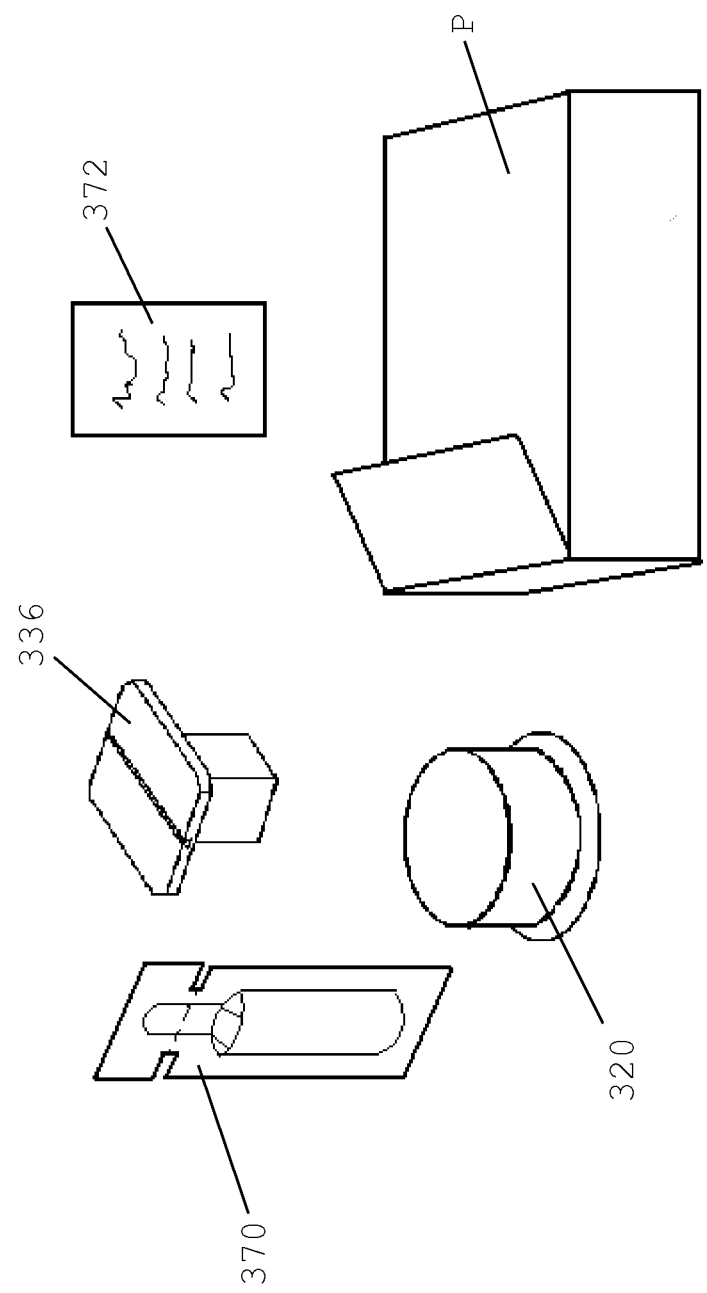
FIG. 30 is a schematic of a kit for preparing a tissue sample for frozen storage.

Suitably, a kit for preparing a tissue sample for frozen storage can be provided. In one embodiment, illustrated in FIG. 30, the kit can include the container 320, a package 370 containing an amount of sacrificial material suitable for placing in the container to support a tissue sample at a position above a bottom of the base 322 of the container, and instructions 372 instructing a user to mount the tissue sample in the container as described above. The amount of sacrificial material in the package 370 is suitably a pre-determined amount sufficient to mount tissue to the container 320 such that the tissue sample is above the level of the base 222 of the container. The sacrificial material can be any bio-inert material as set out above, such as OCT, paraffin, gelatin, saline, buffer, agar, cell culture media, ultrapure water, or other material suitable to support a tissue sample above a bottom of the container. In another embodiment, the kit can include the container 320 prefilled with a sacrificial layer and instructions instructing a user to mount the tissue sample in the container as described above. Suitably, if the container 220 does not include an integral mount, the kit can further include a mount 336 or another suitable mount as described above for use in mounting the container to a slide sectioning device as described above. The kit can also include a package containing an amount of a secondary medium (not shown) for use in rewetting the sacrificial material to mount the tissue if necessary. Suitably, the kit can be contained in a box or other packaging P.

When a sample of the frozen tissue sample is required, the container 320 is removed from cold storage and attached to a slide sectioning device as described above. Depending on the temperature of the container 320 and its contents (which is determined by the maximum freezing temperature of whatever material is used for the sacrificial layer), either a cryotome or a microtome can be used for slide sectioning. For example, if OCT is the fixation medium, a microtome can be used. If saline is the fixation medium, a cryotome can be used. The container 320 is secured to the slide sectioning device, and one or more slide sections are taken. The slides are evaluated and annotated to determine the area of interest of the frozen tissue sample. The container 320 can then be fixated to a tray for coring, as described above. For example, the container 320 can be fixated by the clamping mechanism 114 to the tray 112 for coring by the handheld coring device 10. Alternatively, the container 320 can be fixated to an automatic or robotic coring system for coring. Frozen sample cores can be taken through the frozen tissue sample and down into the sacrificial layer, ensuring that all fibrous membranes are cut and a good frozen aliquot is obtained. After the desired frozen sample cores are taken, the container 320 can be returned to cold storage until another sample is required.

Thus, the container 320 permits a sample to be mounted one time, whether the sample is fresh or frozen, and to remain in a fixed orientation within the container throughout storage, sectioning, and sampling. The container can be removed from cold storage, mounted to a slide sectioning device for sectioning, moved to a cold plate for sampling, and then returned to cold storage. Therefore, handling of the tissue is minimized, thereby reducing the risk of damaging or contaminating the tissue sample, and the process is streamlined. Furthermore, sectioned slides are often stored digitally, and the fixed orientation of the tissue sample within the container permits further sampling based on a stored slide, rather than requiring further sectioning.

Figure 31:
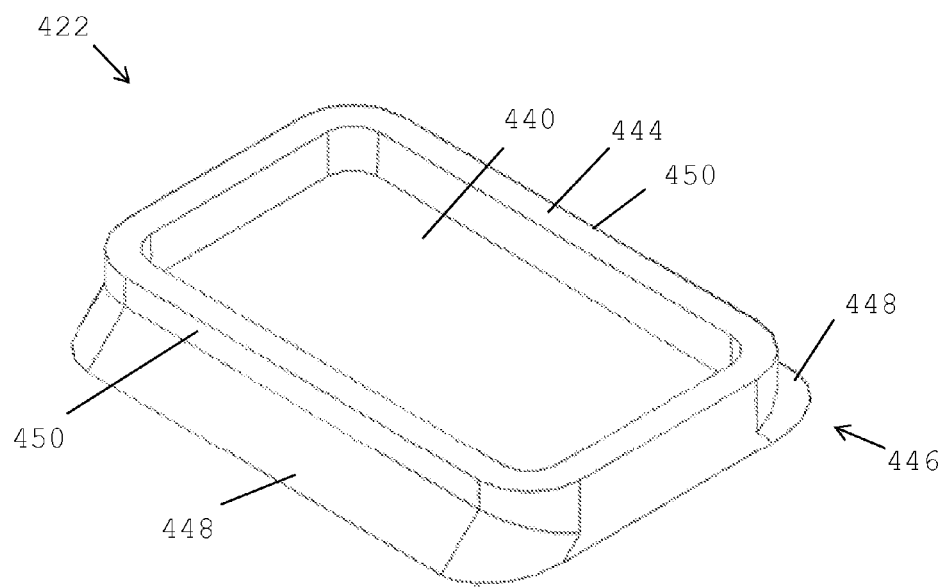
FIG. 31 is a perspective of one embodiment of a tissue carriage.
Figure 32:
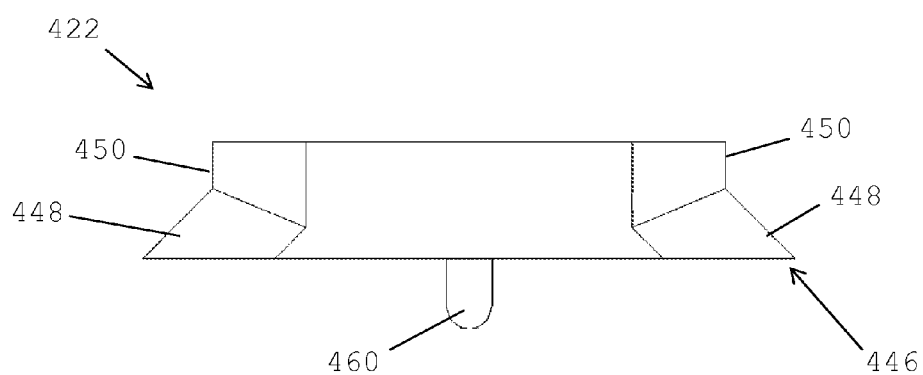
FIG. 32 is a front elevation of the tissue carriage.
Figure 33:
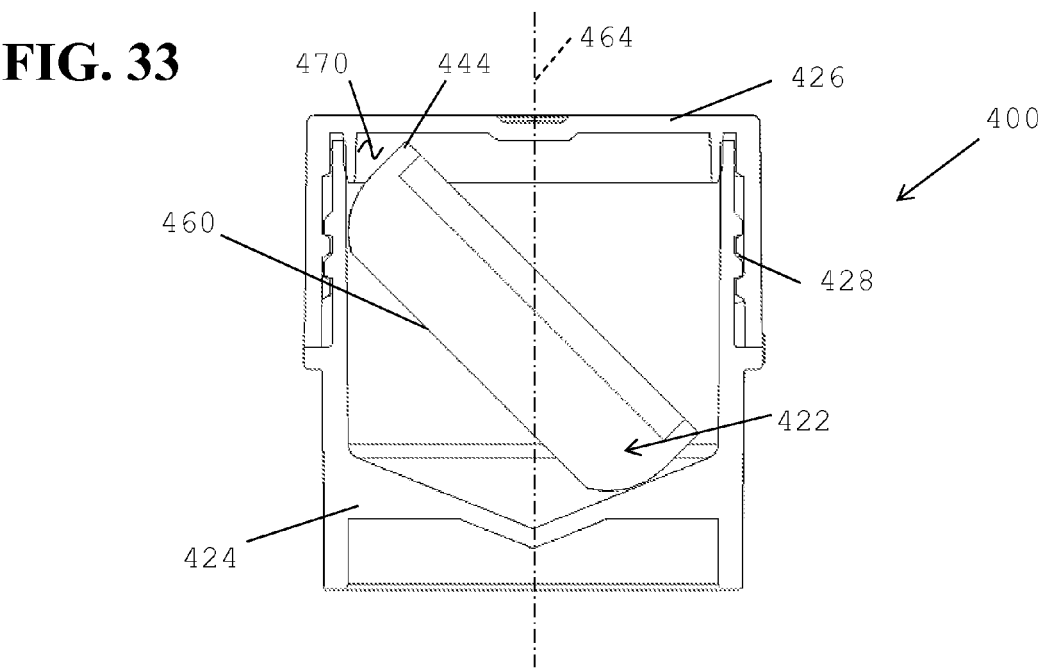
FIG. 33 is a side elevation of the tissue carriage illustrated in FIGS. 31 and 32 enclosed in a container.

FIGS. 31 and 32 illustrate another embodiment of a tissue carriage 422. The tissue carriage 422 can form the base of a container having a lid that attaches to the tissue carriage, as described above. However, as illustrated in FIG. 33, the tissue carriage 422 is suitably part of a system 400 for storing frozen tissue samples including a container 420. In the illustrated embodiment, the container 420 includes a base 424 that is separate from the tissue carriage 422 and a lid 426 that is selectively engageable with the base 424 (e.g., via threads 428) for opening and closing the container. The container can have any shape within the broad scope of the invention. For example, the container is suitably generally cylindrical and suitably has a circular cross-sectional shape. The tissue carriage 422 is sized and shaped to be enclosed in the container, as illustrated in FIG. 33. The tissue carriage 422 is not affixed to the container 420. The tissue carriage 422 and container 420 are suitably configured so the tissue carriage can be removed from the container when it is open just by lifting the tissue carriage straight out of the base 424 of the container.

Referring again to FIGS. 31 and 32, the tissue carriage 422 has a support surface 440 for supporting a sample of frozen tissue 442. The tissue carriage suitably includes a peripheral sidewall 444 extending up from a perimeter of the support surface 440. However, the peripheral sidewall can be omitted without departing from the scope of the invention. The tissue carriage 422 illustrated in FIGS. 31 and 32 has a rectangular perimeter, but the tissue carriage can have other shapes, including without limitation oval and circular, within the scope of the invention.

Figure 34:
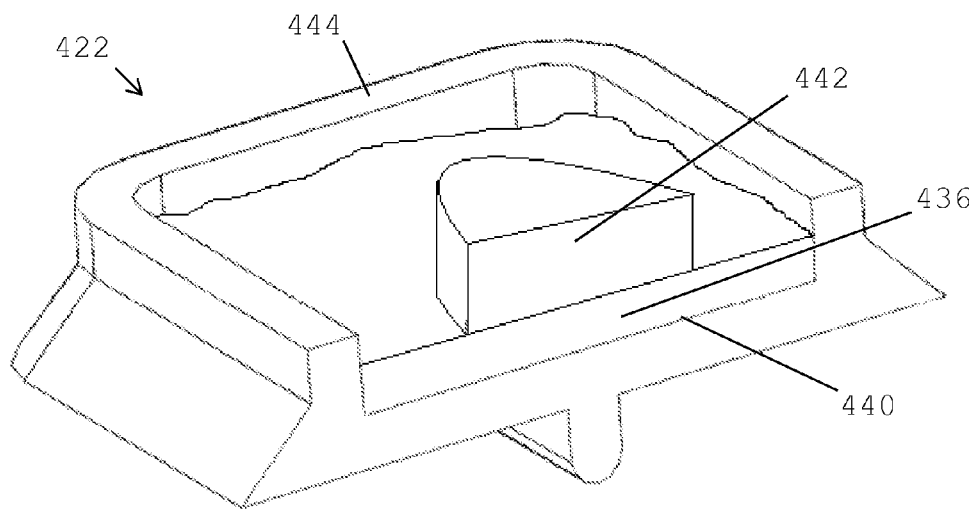
FIG. 34 is a perspective of the tissue carriage of FIGS. 31 and 32 in combination with a sacrificial material and a tissue sample, all of which are illustrated in cross-section.

FIG. 34 shows the tissue carriage 422 in combination with a frozen tissue sample 442 affixed to the support surface 440 of the tissue carriage. As illustrated, a layer of sacrificial material 436, as described above, is positioned between the frozen tissue sample 442 and the support surface 440 and affixes the tissue sample to the support surface.

The tissue carriage 422 includes a coupling 446 for mounting the tissue carriage to a sectioning device for sectioning the frozen tissue 442 while the frozen tissue is supported by the support surface. As illustrated in FIGS. 31-32, the coupling 446 comprises projections 448 extending outwardly from opposite sides 450 of the tissue carriage 422. For example, the projections 448 are suitably outwardly tapered lower ends of the sides 450 configured to make a dovetail connection with a mount 452 having a dovetail groove 454 for mounting the tissue carriage on a sectioning device. The same mount 452 or a similar mount can be used to mount the tissue carriage 422 on a coring device (e.g., the coring system 100 illustrated and described herein) or hold the tissue carriage while a hand-held coring device (e.g., the hand-held coring device 10 described above) is used to take a frozen sample core from frozen tissue 442 affixed to the support surface of the tissue carriage. The sides 450 are suitably generally parallel to one another as illustrated.

Figure 35:
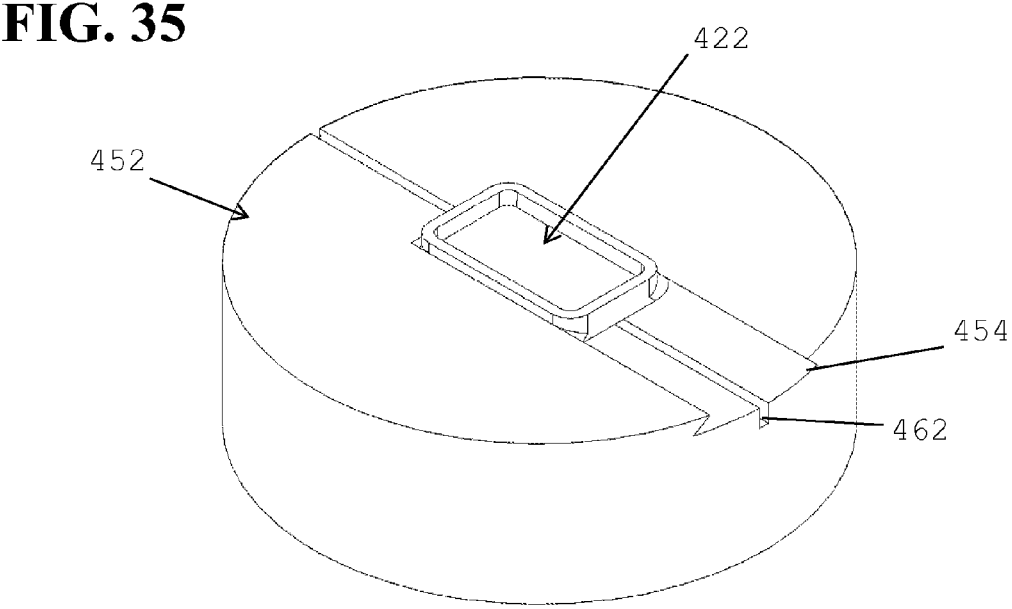
FIGS. 35 and 36 are perspectives of the tissue carriage of FIGS. 31-34 connected to a mount, with FIG. 36 illustrating the tissue carriage and mount in cross-section.
Figure 36:
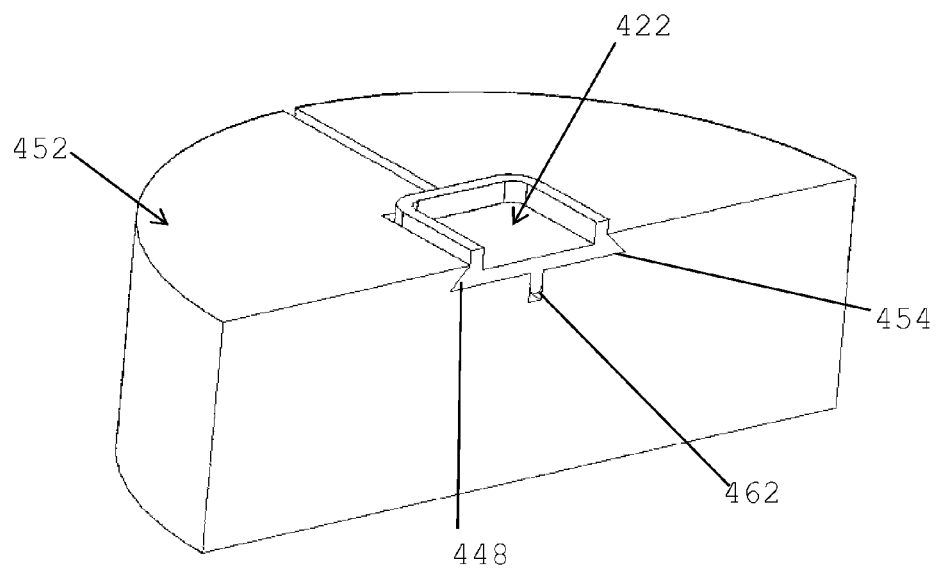

As illustrated in FIGS. 32 and 34, the tissue carriage 422 suitably also includes a rib 460 extending along a surface of the tissue carriage opposite the support surface 440. The rib 460 is positioned to increase stiffness of the support surface 440, for example by increasing stiffness of the entire tissue carriage 422. The rib 460 is sized and shaped to be received in a groove 462 of the mount 452. The rib 460 and groove 462 of the embodiment illustrated in FIGS. 34-36 are configured so the rib could be lifted straight out of the mount 452 (e.g., without sliding the rib out of the end of the groove 462, but for the engagement between the coupling 446 and the mount. However, it is understood the rib can be a dovetail-shaped rail, lollipop-shaped rail, or other shaped-rail that is configured to provide, or enhance, the connection to the mount.

As illustrated in FIG. 33, the tissue carriage 422 is suitably sized and shaped so the support surface 440 must be inclined at an angle relative to a central axis 464 of the container 420 in order for the tissue carriage to fit within the container. For example, the tissue carriage 422 may be dimensioned relative to the container to have a length that exceeds a distance between opposite sides of the container (e.g., a length that exceeds the interior diameter of a container having a circular cross-sectional shape), but which is less than a diagonal distance across the interior space of the container.

Figure 37:
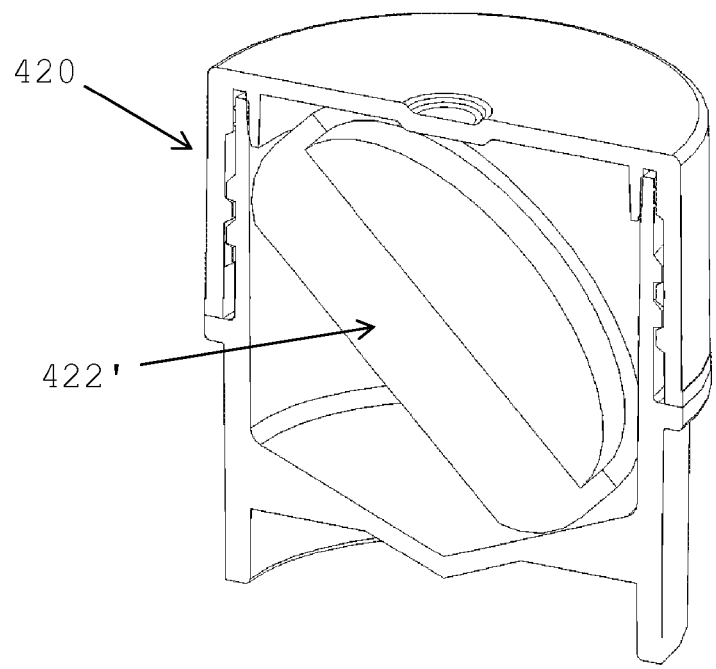
FIGS. 37 and 38 are cross-sections illustrating additional embodiments of a tissue carriage enclosed in a container.
Figure 38:
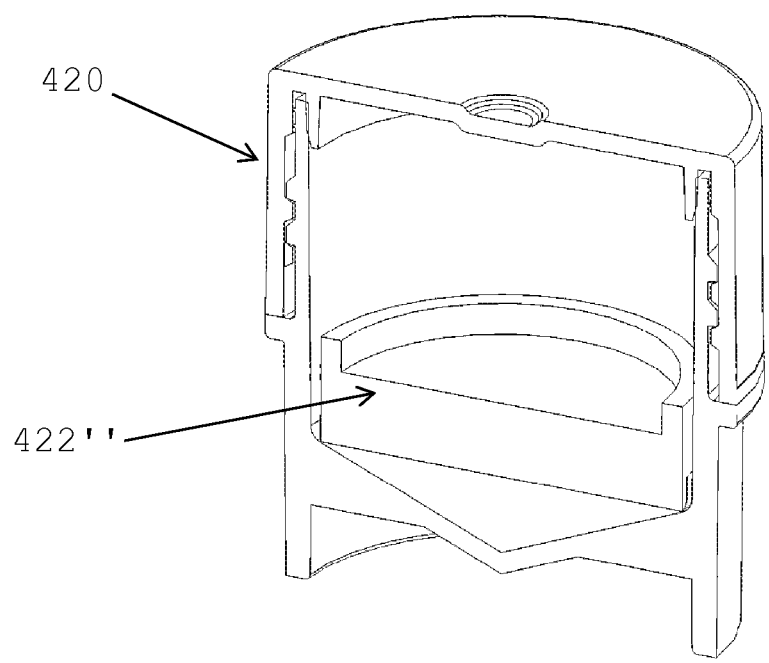

This diagonal arrangement of the tissue carriage 422 allows the size of the support surface 440 to be increased beyond the size that could be accommodated in an arrangement in which the tissue carriage sits flat on the bottom of the container. The area of the support surface can also be increased by changing the shape of the tissue carriage to match a cross-sectional shape of the interior of the container. For example, FIGS. 37 and 38 show tissue carriages 422', 422" that are substantially similar to the tissue carriage 422 described above, except for the shape of the tissue carriages. The tissue carriage 422' in FIG. 37 has an oval-shaped (e.g., elliptically-shaped) support surface 440' that matches the shape of a cross-section of the interior space of the container taken in a plane that is inclined relative to a central axis 464 of the container. For example, the plane may be oriented at an angle generally between about 35 and 55 degrees (e.g., about 45 degrees, as illustrated) relative to the central axis 464 of the container. In the case of the cylindrical container 420 having a circular cross-section, as illustrated, the cross-sectional shape of the interior space taken through an inclined plane is elliptical.

The tissue cartridge 422" in FIG. 38 has a generally circular peripheral shape that matches the cross-sectional shape of the container 420 taken through a non-inclined plane. The tissue carriage 422" can lay flat on the bottom of the container 420. Because the shape of the support surface 440" matches the shape of the container, it is possible to increase the allowable area of the support surface compared to other tissue carriages that do not match the shape of the container. It may be desirable in some cases to have the tissue carriage sit flat in the container. The height of the container 420 can be reduced compared to the container 420 illustrated in FIG. 38 to make more efficient use of space, if desired.

The support surface 440 suitably has an area that is at least about 60 percent of the area of the largest planar surface that can be enclosed in the container, more suitably at least about 70 percent of the largest planar surface that can be enclosed in the container, more suitably at least about 80 percent of the largest planar surface that can be enclosed in the container, and still more suitably at least about 90 percent of the largest planar surface that can be enclosed in the container. This can be achieved by any combination of matching the shape of the tissue carriage to the shape of the interior space, dimensioning the tissue carriage so it must extend diagonally within the interior space, and/or reducing the height of the container.

The diagonal arrangement of the tissue carriage 422 in the container 420, as illustrated in FIG. 33 can also facilitate removal of the tissue carriage 422 from the container. One consequence of the diagonal arrangement of the tissue carriage 422 is that at least a portion of the peripheral sidewall is spaced from the sidewall of the container, which creates a relatively large gap 470 making it easier to grip the tissue carriage 422 by the exterior of the peripheral sidewall 444 to remove the tissue carriage from the container. Referring to the tissue carriage 422" illustrated in FIG. 38, even when the tissue carriage is configured to lay flat at the bottom of the container 420 is can be desirable to dimension the tissue carriage to ensure that at least a portion of the tissue carriage is spaced from a sidewall of the container to form a gap to facilitate removal of the tissue carriage from the container.

According to one embodiment of a method of using the system 400, a tissue sample 442 is affixed to the support surface 440 of the tissue carriage 422. For example, a layer of sacrificial material 436 is suitably placed on the support surface 440 of the tissue carriage 422 and the tissue sample 442 is suitably affixed to the sacrificial material to affix the tissue sample to the support surface. One way to accomplish this is to place a tissue sample 442 that is already frozen onto the sacrificial material 436 under conditions that result in thawing of a thin bottom layer of the tissue followed by subsequent refreezing of that layer to adhere the tissue sample to the tissue carriage. For example, an upper surface of the tissue carriage 422 (e.g., the upper surface of the sacrificial material 436 can be wetted to promote attachment of a frozen tissue sample 442 to the tissue carriage 422. Another example, of affixing a tissue sample 442 to the tissue carriage 422 includes placing unfrozen tissue on the tissue carriage (e.g., on the layer of sacrificial material 436 and freezing the tissue after the container 420 is in frozen storage.

The tissue sample 442 is enclosed in a container, either by securing a lid to the tissue carriage so the lid and tissue carriage together form a container that encloses the tissue sample, or by enclosing the tissue carriage 422 in a separate container 420. For example, enclosing the tissue sample 442 in the container 420 suitably includes orienting the tissue carriage 422 so it is inclined relative to the central axis 464 of the container. If the tissue sample 442 is not already frozen, it freezes in the container 420 while the container is in frozen storage. If the tissue sample 442 is already frozen, it is maintained in its frozen state within the container 420 while it is kept in frozen storage.

Later, when the frozen tissue sample 442 is desired for research, the tissue sample and tissue carriage 422 are removed from the container 420. For example, the lid 426 is removed and the tissue carriage 422 is mounted on the mount 452, which is connected the tissue carriage to a cryotome, microtome, or other sectioning device, to mount the frozen tissue sample 442 on the sectioning device. The slide sectioning device may be positioned in a cold environment (e.g., within a chamber or ante-chamber of the frozen storage system) or it may be in a warmer environment (e.g., "room temperature") within the scope of the invention.

Figure 39:
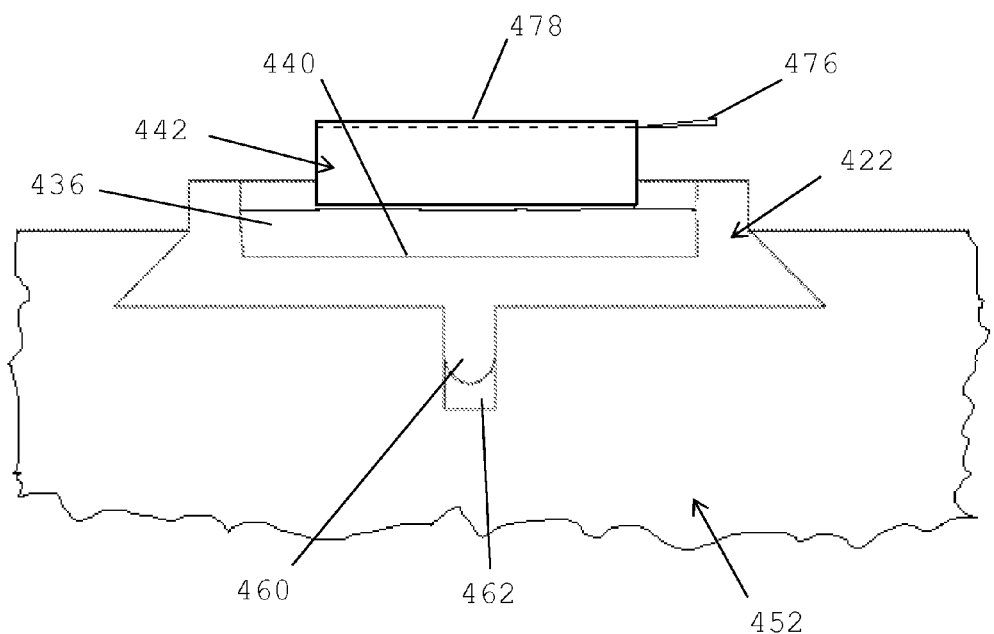
FIGS. 39-41 are schematic illustration of a methods of taking a tissue section from a frozen tissue sample and inserting a coring bit into the frozen tissue sample to obtain a frozen sample core while the sample is affixed to a tissue carriage.

As illustrated in FIG. 39, the frozen tissue sample 442 is sectioned while the frozen tissue remains affixed to the tissue carriage, e.g., to obtain a thin section of the tissue sample that can be mounted on a microscope slide and examined (e.g., by a pathologist or other researcher) to identify one or more features of interest within the tissue sample. As illustrated in FIG. 39, for instance, the blade 476 of the sectioning device cuts a thin layer from the top of the frozen tissue sample 442, which extends above the top of the peripheral sidewall 444 of the tissue carriage 422. The sectioned material 478 is placed on a microscope slide or otherwise analyzed (e.g., according to conventional methods) to identify one or more features of interest in the tissue section. If desired, the frozen tissue sample 442 may be returned to frozen storage by placing the tissue carriage 420 back in the container 420 (or another container) and placing the container back in frozen storage.

However, it may be desirable to conduct further research on material(s) excised from the area(s) of interest within the frozen tissue sample 442. One way to obtain these additional materials within the broad scope of the invention is to use a scalpel to cut the frozen tissue sample into pieces including pieces isolated from the area(s) of interest in the sample. However, this approach does not necessarily preserve the integrity of the remaining portions of the frozen tissue sample 442 and may hinder opportunities to use the same frozen tissue sample 442 for further research.

Figure 40:
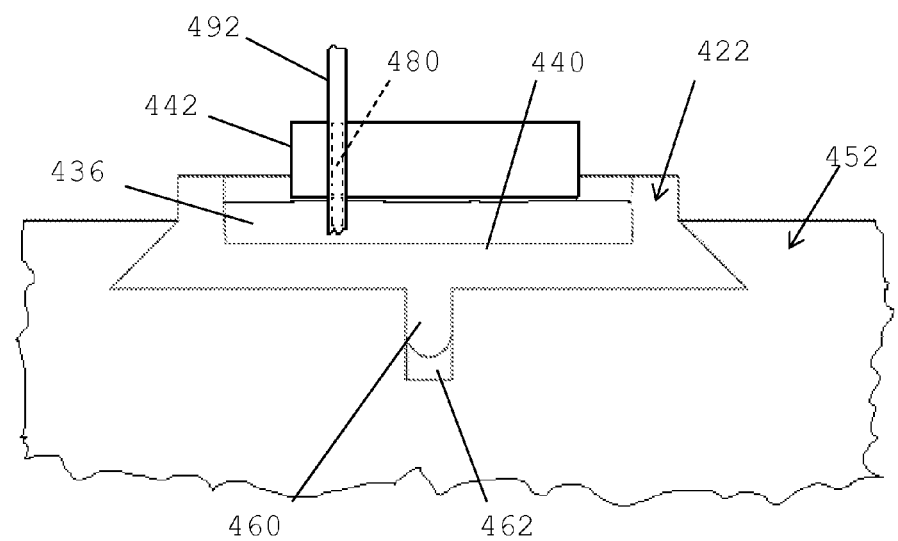
Figure 41:
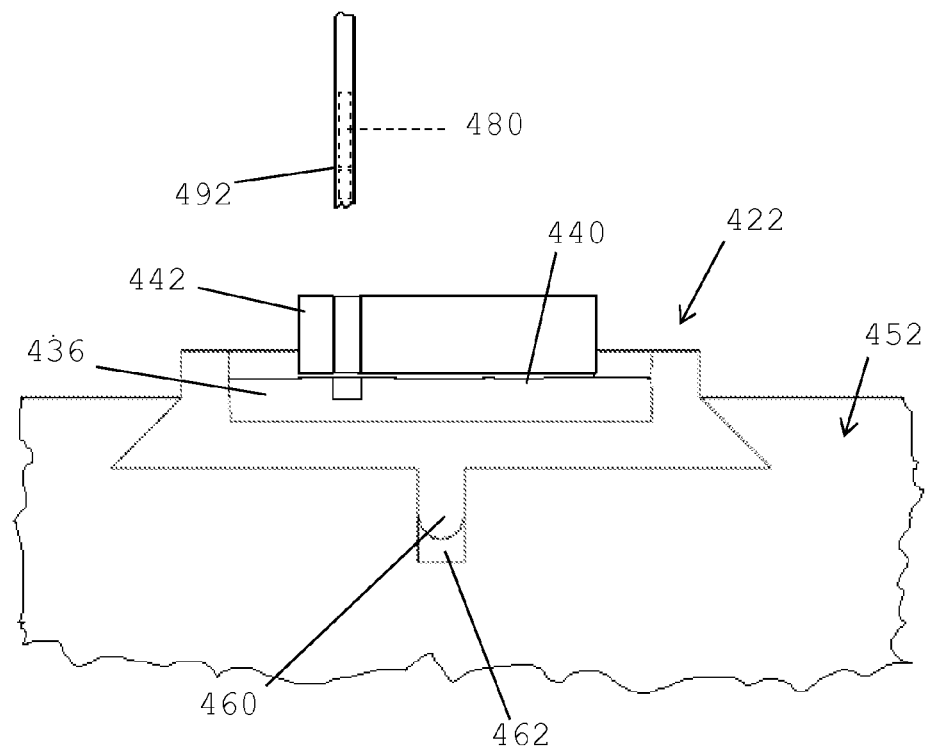
Figure 42:
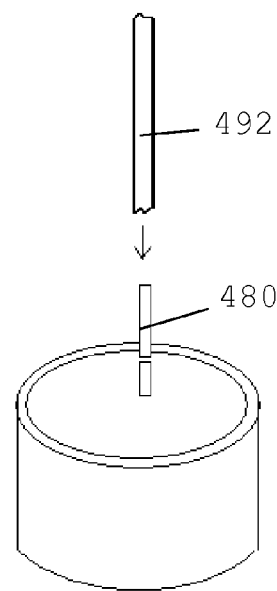

Thus, in the method illustrated in FIGS. 40-42, a coring bit 492 (which can be a single-use coring bit 12, 112 described above or a reusable coring probe) is inserted into the frozen tissue sample 442 while it is affixed to the to the tissue carriage 422 to obtain a frozen sample core 480 from a portion of the sample corresponding to the location of a feature of interest identified during the analysis. For example, the tissue carriage can remain connected to the same mount 452 and the mount can be transferred from the sectioning device to a coring device or the tissue carriage can be transferred to another similar mount at the coring system. It is understood, however, that other options for securing the tissue carriage during the coring operation are within the broad scope of the invention.

Referring to FIG. 40, the coring bit 492 is suitably extended all the way through the frozen tissue sample 442 and into the sacrificial material 436 below the tissue sample. This helps ensure the sample core 480 is completely severed from the remainder of the frozen tissue sample 442. The ability to extend the coring probe 492 into the sacrificial material 436 also facilitates obtaining a full-depth sample core 480 without damaging the tissue carriage 422 or coring system. The sample core 480 is If desired, additional sample cores can be taken from different locations within the frozen tissue sample 442 either reusing a reusable coring probe or using a different single-use coring probe to obtain each particular frozen sample core.

Once all the frozen sample cores 480 that are desired for current research have been obtained, the remaining frozen tissue sample 442 is suitably enclosed in the same container 420 or another container, e.g., in the same manner described above, and returned to frozen storage without separating the remaining frozen tissue sample from the tissue carriage 422. This preserves the option to use one or more portions of the remaining frozen tissue sample 422 in future research. Moreover, the analysis of the initial sectioned material 478 can be preserved (e.g., using electronic storage of an image of the sectioned material along with indicia, such as notes or markings, of the results of the analysis) while the remaining frozen tissue sample is preserved in frozen storage. In some cases this may allow future researchers to rely on the stored information corresponding to the previously-analyzed section 478 from the frozen tissue sample 442 and thereby avoid the steps of sectioning and analyzing the frozen tissue sample each time it is considered for research. Thus, the method can include retrieving the remaining frozen tissue sample 442 from frozen storage after a period of time has elapsed since the frozen tissue sample was sectioned and analyzed and taking additional frozen sample cores 480 from one or more areas of interest in the frozen sample without any further sectioning and/or analysis of the frozen sample. This process can be repeated additional times. This helps preserve the amount of frozen sample material that remains each time the material is used for research. It also reduces cost and time of conducting research using the frozen tissue sample. It is understood, however, that in some cases additional sectioning and analysis may be desired (e.g., to identify features of interest in future research that may not have been recognized during the initial analysis, etc.) and that additional sectioning and analysis of the frozen tissue sample may be conducted without departing from the scope of the invention.

The methods described herein can also preserve integrity of the sample by reducing the number of times the sample is handled. There is no need to contact the frozen tissue sample (except with the blade of the sectioning device and/or the coring bit(s)) once it is affixed to the tissue carriage. The ability to obtain additional frozen sample cores after a significant period of time has elapsed without re-using the sectioning device also helps minimize the amount of handling the sample is subjected to. Moreover, the frozen tissue sample does not need to contact more than one surface (i.e., the surface on the tissue carriage to which it is initially affixed) for the total duration of time it is stored in frozen storage and contact between the frozen tissue sample and other objects can be limited to contact with instruments (e.g., the blade of the sectioning device and/or coring bit of a coring apparatus) that are used to excise smaller samples of material from the frozen tissue sample.

When introducing elements of the present invention of the preferred embodiments thereof, the articles "a", "an", "the", and "said" are intended to mean that there are one or more of the elements. The terms "comprising", "including", and "having" are intended to be inclusive and mean that there may be additional elements other than the listed elements.

In view of the foregoing, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:

1. A single-use coring probe for collecting a frozen aliquot from a frozen biological sample, the single-use coring probe comprising:
   a hollow coring bit for taking a frozen sample core from the frozen biological sample;
   an ejector adapted to eject the frozen sample core taken by the hollow coring bit from the hollow coring bit, the ejector being moveable from a retracted position to an extended position and operable to push a frozen sample core out of the coring bit as it moves from the retracted position to the extended position;
   a locking mechanism adapted to prevent re-use of the single-use coring probe; and
   a coupling adapted to connect the hollow coring bit to a coring device,
   wherein the coupling is adapted to connect the hollow coring bit to a motor coupling adapted to transmit rotation and torque from a motor in the coring device to the hollow coring bit, and wherein the coupling comprises a flange and the motor coupling comprises a magnet having an opening and a magnetic coupling comprising a magnetic support and a plurality of balls, wherein the magnetic field between the magnet and the magnetic support forces the plurality of balls into engagement with a distal surface of the flange of the coring bit coupling, the flange being adapted to be received in the opening of the magnet and secured in the opening by the balls.

2. A single-use coring probe as set forth in claim 1 wherein the locking mechanism is automatically activated upon movement of the ejector to the extended position.

3. A single-use coring probe as set forth in claim 1, wherein the locking mechanism is adapted to prevent movement of the ejector from the extended position toward the retracted position.

4. A single-use coring probe as set forth in claim 1, wherein the ejector does not extend beyond a distal end of the hollow coring bit in the retracted position and the ejector extends beyond the distal end of the hollow coring bit in the extended position.

5. A single-use coring probe as set forth in claim 1, further comprising a coring depth guide positioned on the hollow coring bit, the coring depth guide being adapted to limit the depth to which the hollow coring bit can be inserted into a frozen biological sample.

6. A single-use coring probe as set forth in claim 1 wherein the locking mechanism comprises at least one barb on the ejector adapted to engage an aperture in a sidewall of the hollow coring bit, the barb and aperture being configured to resist movement of the ejector toward the retracted position when the barb is received in the aperture.

7. A single-use coring probe as set forth in claim 1 wherein the hollow coring bit further comprises a frozen sample core retaining system at a distal end of the hollow coring bit to facilitate retention of a frozen sample core within the hollow coring bit.

8. A single-use coring probe as set forth in claim 7 wherein the frozen sample core retaining system comprises at least one tab extending radially inward into a hollow interior of the hollow coring bit.

9. A single-use coring probe as set forth in claim 8 wherein the tab is angled so it extends away from a distal end of the hollow coring bit as it extends radially inward.

10. A single-use coring probe as set forth in claim 7 wherein the frozen sample core retaining system comprises at least one finger movable from a first position radially inward to a second position, the finger extending radially inward into the hollow coring bit through an aperture in a sidewall of the hollow coring bit in the second position.

11. A single-use coring probe as set forth in claim 10 wherein the frozen sample core retaining system further comprises a sleeve adapted to receive a portion of the hollow coring bit, the at least one finger being positioned on a distal end of the sleeve.

12. A single-use coring probe as set forth in claim 7 wherein the frozen sample core retaining system comprises a surface on an interior of the hollow coring bit that has been treated to increase resistance to sliding of a frozen sample core on the treated surface compared to resistance to sliding of the frozen sample core on an untreated surface of hollow coring bit.

13. A single-use coring probe as set forth in claim 12 wherein the treated surface has been subjected to process that increases roughness of the treated surface relative to the untreated surface.

* * * * *